United States Patent
Yamashita et al.

(10) Patent No.: US 9,972,766 B2
(45) Date of Patent: May 15, 2018

(54) PIEZOELECTRIC TRANSDUCER, ULTRASONIC PROBE, AND PIEZOELECTRIC TRANSDUCER MANUFACTURING METHOD

(71) Applicant: Toshiba Medical Systems Corporation, Otawara-shi (JP)

(72) Inventors: Yohachi Yamashita, Yokohama (JP); Noriko Yamamoto, Yokohama (JP); Yasuharu Hosono, Kawasaki (JP); Kazuhiro Itsumi, Tokyo (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 445 days.

(21) Appl. No.: 14/840,115

(22) Filed: Aug. 31, 2015

(65) Prior Publication Data
US 2015/0372219 A1 Dec. 24, 2015

(30) Foreign Application Priority Data
Mar. 25, 2013 (JP) ................................ 2013-062250

(51) Int. Cl.
*H01L 41/08* (2006.01)
*H01L 41/257* (2013.01)
(Continued)

(52) U.S. Cl.
CPC ............ *H01L 41/08* (2013.01); *A61B 8/4444* (2013.01); *B06B 1/067* (2013.01);
(Continued)

(58) Field of Classification Search
CPC ...... H01L 41/08; H01L 41/257; H01L 41/187
(Continued)

(56) References Cited

U.S. PATENT DOCUMENTS 5,402,791 A * 4/1995 Saitoh ................. B06B 1/0648
252/62.9 PZ
2006/0079785 A1* 4/2006 Hosono ................. A61B 8/4281
600/459
(Continued)

FOREIGN PATENT DOCUMENTS

JP 09-083038 A 3/1997
JP 3251727 B2 1/2002
(Continued)

OTHER PUBLICATIONS

International Search Report dated Apr. 28, 2014 in PCT/JP2014/058013 filed Mar. 24, 2014 with English translation.
(Continued)

*Primary Examiner* — J. San Martin
(74) *Attorney, Agent, or Firm* — Oblon, McClelland, Maier & Neustadt, L.L.P.

(57) ABSTRACT

According to embodiment, a piezoelectric transducer includes a polarized single crystal piezoelectric body comprising a lead complex perovskite compound containing niobium oxide and at least one of magnesium oxide and indium oxide and including a first plane whose crystal orientation is [100] and a second plane which faces the first plane and whose crystal orientation is [100], and first electrode provided on the first plane side of the body and a second electrode provided on the second plane side of the body. A ratio of a second FWHM of diffracted X-rays at the Miller index (400) of the body to a first FWHM of diffracted X-rays at the miller index (400) of the body which is unpolarized or has undergone depolarization processing is not less than 0.22 and not more than 0.4.

12 Claims, 9 Drawing Sheets

(51) Int. Cl.
*H01L 41/41* (2013.01)
*H01L 41/187* (2006.01)
*H01L 41/338* (2013.01)
*B06B 1/06* (2006.01)
*A61B 8/00* (2006.01)

(52) U.S. Cl.
CPC ........ *H01L 41/1875* (2013.01); *H01L 41/257* (2013.01); *H01L 41/338* (2013.01); *H01L 41/41* (2013.01); *Y10T 29/43* (2015.01)

(58) Field of Classification Search
USPC .......................................................... 310/334
See application file for complete search history.

(56) References Cited

U.S. PATENT DOCUMENTS

| 2006/0091353 | A1 | 5/2006 | Matsushita et al. |
| 2009/0091215 | A1 | 4/2009 | Aoki et al. |
| 2014/0062261 | A1* | 3/2014 | Yamamoto ............ B06B 1/0622 310/334 |

FOREIGN PATENT DOCUMENTS

| JP | 2006-156976 A | 6/2006 |
| JP | 3987744 B2 | 10/2007 |
| JP | 2008-047693 A | 2/2008 |
| JP | 2009-094139 A | 4/2009 |
| JP | 2009-188104 A | 8/2009 |
| JP | 2013-26682 A | 2/2013 |

OTHER PUBLICATIONS

Written Opinion dated Apr. 28, 2014 in PCT/JP2014/058013 filed Mar. 24, 2014.
Ke-Pi Chen, et al., "Electric-field-induced phase transition in <001>-oriented $Pb(Mg_{1/3}Nb_{2/3})O_3$-$PbTiO_3$ single crystals" Journal of Physics: Condensed Matter, vol. 14., No. 29, 2002, pp. L571-L576.
C.-S. Tu, et al., "Phase stability after an electric-field poling in $Pb(Mg_{1/3}Nb_{2/3})_{1-x}Ti_xO_3$ crystals" The American Physical Society, Rapid Communications, Physical Review B, vol. 70, 2004, 4 pages.
Japanese Office Action dated Aug. 30, 2016 in Patent Application No. 2013-062250 (without English Translation).

* cited by examiner

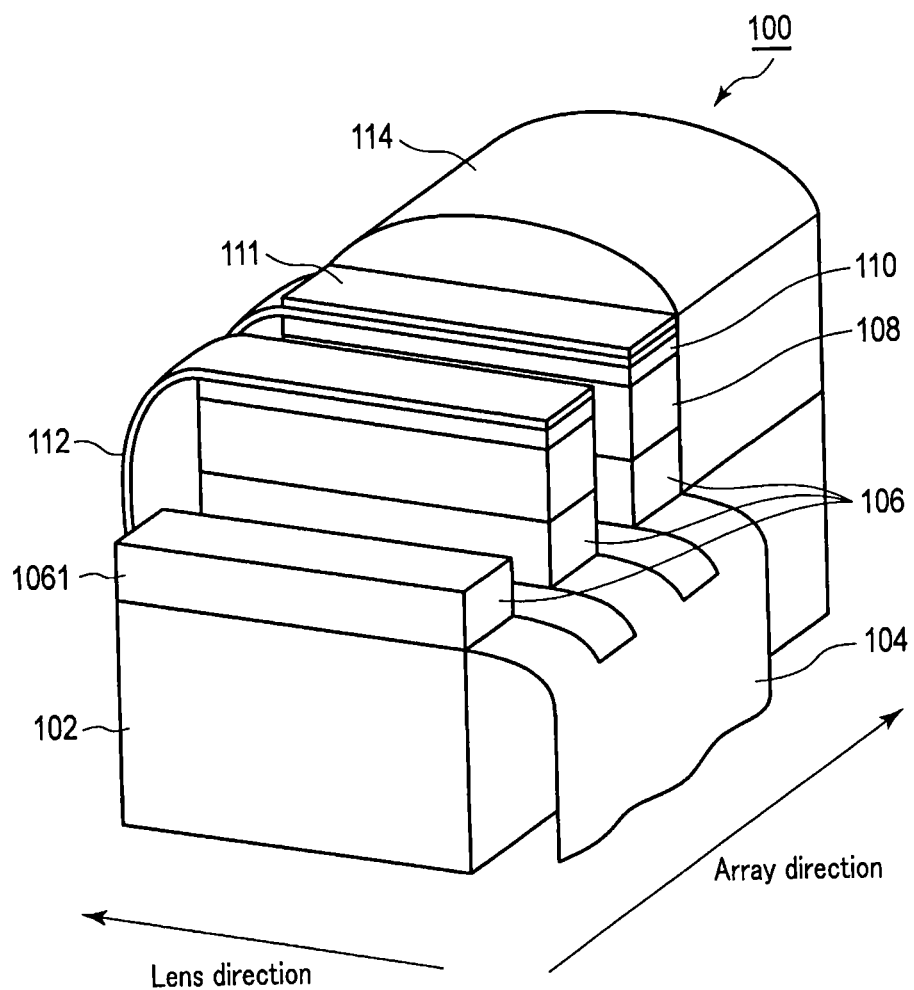
F I G. 10

PIEZOELECTRIC TRANSDUCER, ULTRASONIC PROBE, AND PIEZOELECTRIC TRANSDUCER MANUFACTURING METHOD

CROSS-REFERENCE TO RELATED APPLICATIONS

This application is a Continuation application of PCT Application No. PCT/JP2014/058013, filed Mar. 24, 2014 and based upon and claims the benefit of priority from the Japanese Patent Application No. 2013-062250, filed Mar. 25, 2013, the entire contents of all of which are incorporated herein by reference.

FIELD

Embodiments described herein relate generally to a piezoelectric transducer, an ultrasonic probe, and a piezoelectric transducer manufacturing method.

BACKGROUND

A medical ultrasonic diagnostic apparatus and an ultrasonic image examination apparatus such as a fishfinder or sonar transmit ultrasonic waves to an object via an ultrasonic probe, and visualize the interior of the object based on the reflection signal (echo signal) generated by reflected waves from the interior of the object. The medical ultrasonic diagnostic apparatus and the ultrasonic image examination apparatus mainly use an electronic operation type array ultrasonic probe having an ultrasonic transmission/reception function.

A general ultrasonic probe includes a backing member, piezoelectric transducers each joined on the backing member and having electrodes formed on the two surfaces of a piezoelectric body, and acoustic matching layers joined on the piezoelectric transducers. The piezoelectric transducers and the acoustic matching layers are formed into a plurality of channels by array machining. An acoustic lens is formed on the acoustic matching layers. The electrodes of the piezoelectric transducers corresponding to the respective channels are connected to the apparatus main body of each of the medical ultrasonic diagnostic apparatus and the ultrasonic image examination apparatus via a control signal board (FPC (Flexible Printed Circuit)) and cables.

BRIEF DESCRIPTION OF THE DRAWINGS

FIG. 10 is a view showing an example of the structure of an ultrasonic probe according to this embodiment.

DETAILED DESCRIPTION

Figure 1:
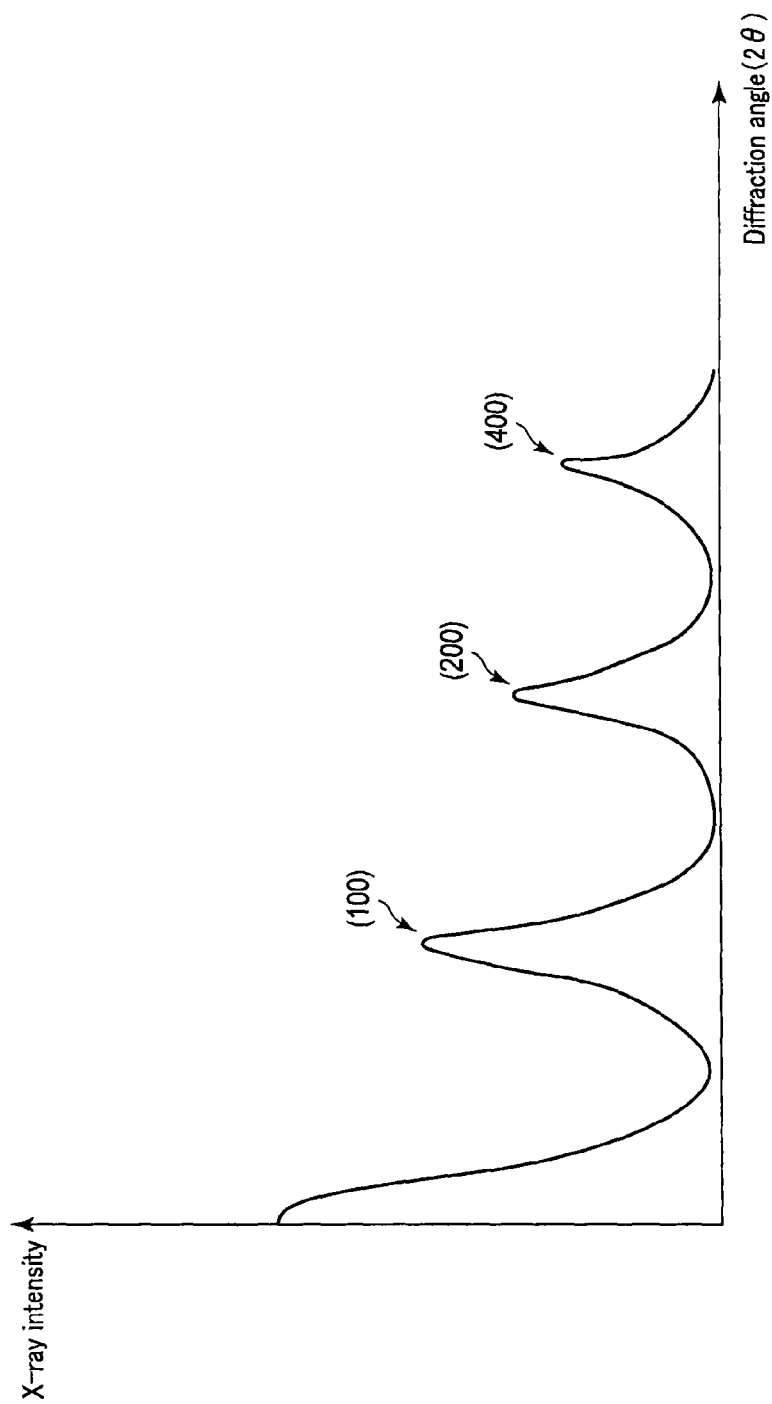
FIG. 1 is a graph showing an example of an X-ray intensity distribution with respect to diffraction angles at the time of X-ray diffraction according to this embodiment.

In general, according to one embodiment, a piezoelectric transducer includes a polarized single crystal piezoelectric body, a first electrode and a second electrode.

The polarized single crystal piezoelectric body includes a lead complex perovskite compound containing niobium oxide and at least one of magnesium oxide and indium oxide. The polarized single crystal piezoelectric body includes a first plane whose crystal orientation is [100] and a second plane which faces the first plane and whose crystal orientation is [100].

The first electrode is provided on the first plane side of the single crystal piezoelectric body. The second electrode is provided on the second plane side of the single crystal piezoelectric body.

A ratio of a second FWHM of diffracted X-rays at the Miller index (400) of the single crystal piezoelectric body to a first FWHM of diffracted X-rays at the miller index (400) of the single crystal piezoelectric body which is unpolarized or has undergone depolarization processing is not less than 0.22 and not more than 0.4.

Each piezoelectric transducer of an ultrasonic probe is an active component which transmits/receives ultrasonic waves. Each piezoelectric transducer is required to have the property of being large in dielectric constant and piezoelectric constant and small in dielectric loss. In addition, dielectric characteristics such as dielectric constant and dielectric loss and piezoelectric characteristics such as piezoelectric constant are required to be homogenous within each piezoelectric transducer and between a plurality of piezoelectric transducers. In addition, the center frequency of transmission ultrasonic waves from such an ultrasonic probe is, for example, 2 MHz or more and 10 MHz or less. For this reason, a piezoelectric transducer generally has a thickness of about 0.05 mm or more and 0.5 mm or less.

Lead zirconate titanate (PZT)-based piezoelectric ceramic has been used as a material for piezoelectric transducers since the 1970s. A high-performance piezoelectric single crystal having a lead complex perovskite structure has begun to be used as a material for piezoelectric transducers since around 2005. A high-performance piezoelectric single crystal having a lead complex perovskite structure is formed from a relaxor-based lead complex perovskite compound composed of 5 mol % or more and 45 mol % or less of lead titanate (PbtiO$_3$) and 55 mol % or more and 95 mol % or less of Pb(B1, Nb)O$_3$ (wherein B1 is at least one of magnesium, zinc, indium, scandium, and the like). Note that a piezoelectric single crystal may have 30 mol % or less of lead zirconate.

In the related art, a single crystal having a lead complex perovskite structure having a composition such as [Pb(Mg, Nb)O$_3$]$_{(1-x)}$·[Pb(TiO$_3$)]$_{(x)}$ (to be referred to as PMN-PT hereinafter): (x=0.26 or more and 0.29 or less) is a pseudo-cubic crystal. The above piezoelectric single crystal has a dielectric constant of 5,000 or more at 25° C. In addition, the specific dielectric constant of a single crystal having a lead complex perovskite structure at a transformation temperature Trt between a pseudo-cubic crystal and tetragonal crystal is 2.5 times or more that of PZT-based piezoelectric ceramic at 25° C.

Another related art discloses that applying a DC electric field to a zinc lead niobate-lead titanate Pb(Zn$_{1/3}$, Nb$_{2/3}$)O$_3$—Pb(TiO$_3$) (to be referred to as PZN-PT hereinafter) while lowering a high temperature equal to or higher than the phase transition temperature can control the domain size in the range of 8 μm to 20 μm in accordance with conditions. In this method, the domain is formed in a direction parallel to the electrode surface.

The crystal orientations of all the planes of a crystal of a piezoelectric element used for a piezoelectric transducer are [100]. A piezoelectric element with the crystal orientations of all the planes being [100] is mainly used for an ultrasonic probe. In addition, a material obtained by adding manganese oxide to the above piezoelectric element is used for an ultrasonic probe. The piezoelectric element is polished to a thickness of 0.05 or more and 0.5 mm or less. Thereafter, electrodes are formed on the upper and lower surfaces of the piezoelectric element. More specifically, silver (Ag), gold (Au), nickel (Ni), chromium (Cr), palladium (Pd), and the like are provided on the upper and lower surfaces of the piezoelectric element by a baking method, sputtering method, deposition method, wet plating method, or the like. A DC electric field of 0.2 kV/mm or more and 3 kV/mm or less is applied to the resultant structure in the temperature range from room temperature to 200° C. for about 1 min or more and 100 min or less. The piezoelectric element is completed by polarization processing performed by the application of the DC electric field.

For example, in order to provide a piezoelectric single crystal with high sensitivity and resolution, its manufacturing method, a piezoelectric element, and an ultrasonic probe, the piezoelectric transducer is sometimes polarized by a DC electric field of 1 kV/mm while the transducer is cooled from 200° C. to 40° C.

In addition, for example, there is available a piezoelectric element with the electromechanical coupling coefficient k33 in the longitudinal vibration mode in the polarization direction being 80.2% or more (k33≥80.2%) and the piezoelectric distortion constant d33 being 960 pC/N or more (d33≥960 pC/N). This piezoelectric element is formed from 0.91PZN-0.09PT. In addition, in this piezoelectric element, the electromechanical coupling coefficient k31 in the transverse vibration mode in a direction perpendicular to the polarization direction is 74% or more (k31≥74%) and the piezoelectric distortion constant d31 is 1263 pC or more (d31≥1263 pC/N). Furthermore, the piezoelectric element has a feature that the value of a frequency constant (fc31=fr·L) as the product of the resonance frequency (fr) of the transverse vibration mode in a direction perpendicular to the polarization direction concerning k31 and the length (L) of the piezoelectric element in the vibration direction is 609 Hz·m or less (fc 31≤609 Hz·m). A piezoelectric transducer using the piezoelectric element is called a domain-controlled piezoelectric single crystal transducer. The domain-controlled piezoelectric single crystal transducer is prepared as follows. First of all, an auxiliary electrode is provided on a piezoelectric element. The auxiliary electrode is temporarily polarized by a direct current, alternate current, and corona discharge. The auxiliary electrode is then peeled off. A main electrode is provided on another surface different from the surface on which the auxiliary electrode is provided. The domain-controlled piezoelectric single crystal transducer is completed by applying a DC voltage again.

In addition, a piezoelectric transducer is prepared by another piezoelectric transducer manufacturing method, that is, by polarizing an organic piezoelectric material (urea, polyester, or polyamide) provided with a sheet of inorganic material fine particles by applying a direct current, alternate current, and corona discharge.

Furthermore, when the intensity of a DC polarization electric field applied to a [100] plate of a 0.7PMN-0.3PT single crystal is changed, the X-ray intensity at the (400) diffraction angle (2θ) is measured. When the intensity of the polarization electric field is 4 kV/cm, the FWHM (Full Width at Half Maximum) is 0.44°. This value is smaller than the value (0.56°) of the FWHM of an unpolarized product. When the intensity becomes 13 kV/cm upon an increase in voltage, the diffraction angle decreases. That is, the c-axis lattice spacing increases. In addition, the position of the diffraction angle 2θ is 87.5°, which has not changed before and after polarization. Furthermore, the peak height has decreased from 1300 to 1000 due to polarization. Moreover, a ratio W1/W of an FWHM W1 of a polarized product to an FWHM W of an unpolarized product is 0.785. A ratio C1/C of a diffraction angle C1 of the polarized product to a diffraction angle C of the unpolarized product is 1.0000.

In addition, in (1−x)PMN-xPT, on a [100] plate of each of single crystals with x=0.24, 0.26, 0.27, 0.29, and 0.35, the X-ray intensities are measured at the (002) diffraction angle (2θ) before and after polarization. In the case of the crystal with x=0.24 mol %, when the intensity of a polarization electric field is 6 kV/cm, the diffraction angle shifts by about 0.1°. At this time, the c-axis lattice spacing decreases. When the intensity becomes 13 kV/cm upon an increase in voltage, the diffraction angle decreases. That is, the c-axis lattice spacing increases. In addition, when x=0.26 or more and 0.35 or less, applying an electric field will increase the c-axis lattice spacing. The ratio W1/W of the FWHM W1 of the polarized product of the single crystal with x=0.24 to the FWHM W of the unpolarized product is 0.8529. In addition, the ratio C1/C of the diffraction angle C1 of the polarized product to the diffraction angle C of the unpolarized product is 1.0034.

When, however, known piezoelectric single crystals are used for medical ultrasonic transducers, the following problems arise. For example, heat is generated due to a lack in dielectric constant, a lack in piezoelectric constant d33, and a large dielectric loss, large variation in sensitivity characteristic between channels caused by variations in dielectric characteristic and piezoelectric characteristic inside each piezoelectric transducer. In addition, when such single crystals are used for a sonar and the like, the sensitivity characteristics have not reached a satisfactory level.

An X-ray diffraction phenomenon will be described below with reference to the accompanying drawings.

FIG. 1 is a graph showing an example of an X-ray diffraction measurement result according to this embodiment. As shown in FIG. 1, the X-ray diffraction measurement result is obtained as the distribution of X-ray intensities (cps: Count per second) with respect to diffraction angles (2θ). X-ray diffraction angles according to this embodiment were measured by the following method.

The apparatus used to measure X-ray diffraction is, for example, an X-ray diffraction apparatus (ATX-G) available from Rigakudenki. An X-ray source is a Cukα ray source (a parallel beam system using a multilayer mirror: divergence angle of 0.05°). The outputs are a tube voltage of 50 kV and a tube current of 300 mA. The slit system is 1 mmw×10 mmh-Ge 220_2 crystal-0.02 mmw×5 mmh-(SPL)-0.1 mmw×5 mmh-0.2 mmw.

The method used to obtain measurement results on this X-ray diffraction is the θ/2θ method. In the θ/2θ method, the scanning scheme is 2θ/ω continuous scanning. The measurement range is 98° or more and 102° or less. The measurement skip is 0.005°. The scanning speed is 0.25°/min. A diffraction line as a measurement target is a diffraction line concerning the Miller index (400). The method used to determine an X-ray intensity based on an X-ray diffraction measurement result is an FWHM averaging method.

As shown in FIG. 1, as the diffraction angle increases, the X-ray intensity decreases. The X-ray diffraction measurement results in this embodiment reside near the peak (the diffraction angle range of 98° or more and 102° or less) of the Miller index (400).

Figure 2:
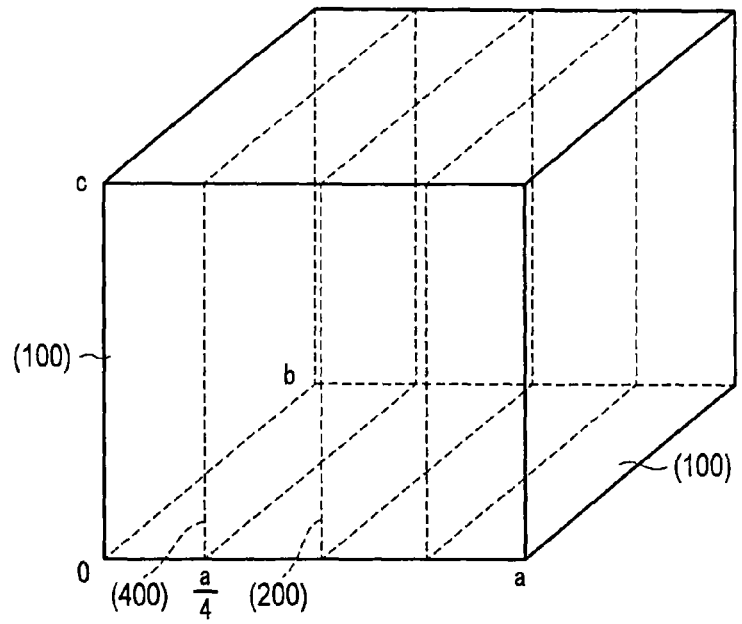
FIG. 2 is a view for explaining the Miller index (400) at the time of X-ray diffraction according to this embodiment.

FIG. 2 is a view for explaining the Miller index (400). Referring to FIG. 2, a, b, and c respectively represent the axes associated with a unit cell of a crystal as a measurement target. Referring to FIG. 2, (400) is a plane which passes through a point a/4 on the a-axis and is parallel to the b-axis and the c-axis. The X-ray diffraction measurement results in this embodiment are associated with the intensities of X-rays diffracted by the (400) plane.

A piezoelectric transducer preparing method, a piezoelectric transducer, an ultrasonic probe, and an ultrasonic probe manufacturing method according to this embodiment will be described below with reference to the accompanying drawings.

The piezoelectric transducer according to this embodiment is prepared by the following method.

Figure 3:
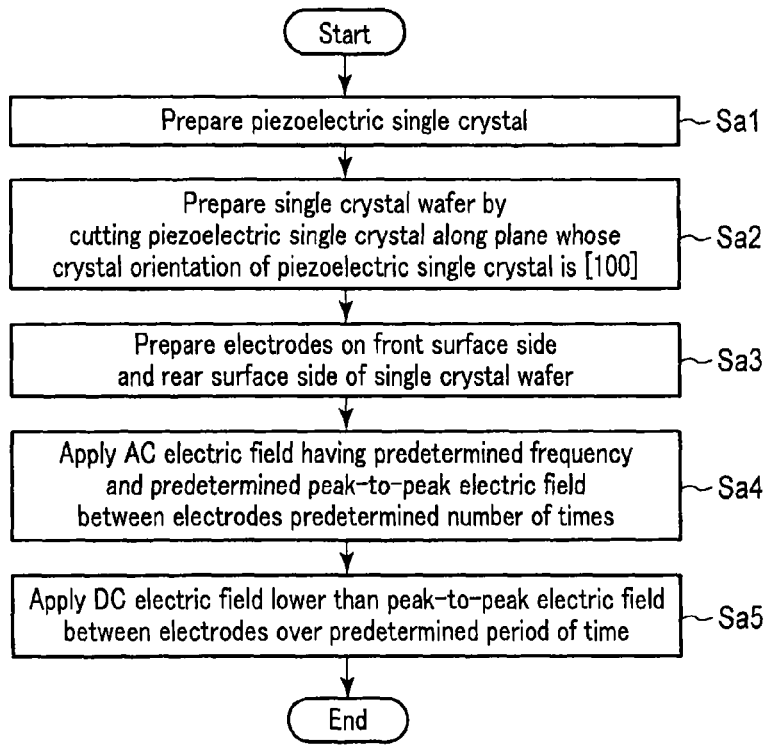
FIG. 3 is a flowchart showing a procedure for manufacturing a piezoelectric transducer according to this embodiment.

FIG. 3 is a flowchart showing a procedure for manufacturing the piezoelectric transducer according to this embodiment. A plurality of raw materials are blended at predetermined ratios to manufacture a piezoelectric single crystal containing lead magnesium niobate ($Pb(Mg_{1/2}Nb_{2/3})O_2$ (to be referred to as PMN hereinafter), lead zinc niobate ($Pb(Zn_{1/2}Nb_{2/3})O_3$ (to be referred to as PZN hereinafter), lead indium niobate ($Pb(In_{1/2}Nb_{1/2}))O_2$ (to be referred to as PIN hereinafter), and lead titanate ($PbTiO_3$) (to be referred to as PT hereinafter). The raw materials used are 99.9% or more of $Pb_3O_4$, $MgO$, $Nb_2O_5$, $ZnO$, $In_2O_3$, and $TiO_2$. These raw materials are weighted. The plurality of weighted raw materials are mixed in a wet state by using a ball mill, a zirconia mill, and distilled water. The plurality of mixed raw materials (to be referred to as the raw material mixture hereinafter) are dried. The dried raw material mixture is calcined several times at 850° C. or higher and 950° C. or lower. A raw material powder is prepared by this calcination.

A water-soluble binder such as polyvinyl alcohol (PVA) is added to the prepared raw material powder at 5% or more and 10% or less of the raw material powder. The raw material powder added with the binder is molded into a predetermined shape by using a press machine. After the molding, a debinding step is executed at 500° C. over several hours. The raw material powder having undergone the debinding step is baked at 1,100° C. or higher and 1,300° C. or lower over several hours. The baked raw material powder will be referred to as ceramic hereinafter.

Ceramic has a diameter of 25 mm or more and 50 mm or less, and is charged into a platinum crucible having a size of 100 mm or more and 200 mm or less. Note that in order to lower the melting point of the ceramic, a small amount of lead oxide or boron oxide is sometimes added. A single crystal as a seed for a [100] plate or [110] plate with the same composition is arranged on the lower portion of the platinum crucible. The [100] plate or [110] plate of the single crystal seed has a length of 20 mm or more and 70 mm or less. The upper portion of the platinum crucible into which the ceramic, the seed, and the like are charged is sealed by welding. The internal temperature of the sealed platinum crucible is held at 1,100° C. or higher and 1,400° C. or lower over 5 hr or more and 15 hr or less. This melts the ceramic in the platinum crucible. In order to prevent the seed placed on the lower portion of the platinum crucible from being melted, a temperature gradient of 20° C./cm or more and 60° C./cm or less is provided starting from the lower portion to the upper portion of the platinum crucible.

Subsequently, in order to grow a long single crystal, the temperature gradient in the platinum crucible is decreased at a rate of 0.2 mm/hr or more and 0.6 mm/hr or less. Crystal growth is executed in a total of 10 days or more and 30 days or less. This prepares a piezoelectric single crystal ingot.

That is, the prepared piezoelectric single crystal ingot contains at least lead titanate ($PbTiO_3$) and a relaxor-based lead complex perovskite compound ($Pb(B1, B2)O_3$): (wherein B1 is at least one of magnesium and indium, and B2 is niobium). Methods of manufacturing the above piezoelectric single crystal ingot include a flux method, a melt Bridgman method, a TSSG method (Top Seeded Solution Growth), a horizontal melt Bridgman method, and a CZ method (Czochralski method). This embodiment is not limited to the above piezoelectric single crystal ingot manufacturing method. A piezoelectric single crystal is prepared by any of the above methods (step Sa1).

A lead complex perovskite compound has a phase transition temperature (to be referred to as a Trt hereinafter) from a rhombohedral system to a tetragonal system, a phase transition temperature (to be referred to as a Trm hereinafter) from a rhombohedral system to a monoclinic system, and a phase transition temperature (to be referred to as a Tmt hereinafter) from a monoclinic system to a tetragonal system in the range of 80° C. or higher and 150° C. or lower. If the phase transition temperature is lower than 80° C., the temperature dependence characteristics of electrical characteristics such as dielectric constant and binding coefficient become conspicuous, as will be described later. If the phase transition temperature exceeds 150° C., a desired dielectric constant cannot be obtained at room temperature, as will be described later. For the above reasons, the phase transition temperature range is preferably 80° C. or higher and 150° C. or lower.

More specifically, a lead complex perovskite compound contains 67 mol % or more and 74 mol % or less of lead magnesium niobate or lead indium niobate and 26 mol % or more and 33 mol % or less of lead titanate. This is because if the ratio of lead titanate to a lead complex perovskite compound is less than 26 mol %, a high dielectric constant and binding coefficient cannot be obtained. In addition, if the ratio of lead titanate to a lead complex perovskite compound exceeds 33 mol %, the phase transition temperatures (Trt, Trm, and Tmt) become 80° C. or lower, and the temperature dependence characteristics of dielectric constant and binding coefficient become conspicuous especially at room temperature to 80° C. For the above reasons, in order to maintain a high dielectric constant and binding coefficient and reduce the above temperature dependence characteristics at room temperature to 80° C., it is necessary to set the ratio of lead titanate to a lead complex perovskite compound to 26 mol % or more and 33 mol % or less.

In addition, the lead complex perovskite compound may contain lead indium niobate, lead magnesium niobate, and lead titanate. That is, the lead complex perovskite compound contains 15 mol % or more and 50 mol % or less of lead indium niobate, 24 mol % or more and 59 mol % or less of lead magnesium niobate, and 26 mol % or more and 33 mol % or less of lead titanate, thus totaling to 100 mol %. That is, in the case of $Pb[\{(Mg_{1/3}Nb_{2/3})y(In_{1/2}Nb_{1/2})z\}Tix]O_3$, x=0.26 or more and 0.33 or less, y=0.24 or more and 0.59 or less, z=0.15 or more and 0.50 or less, x+y=0.67 or more and 0.74 or less, and x+y+z=1.

If the ratio of lead titanate to a lead complex perovskite compound is less than 26 mol %, a necessary dielectric constant cannot be obtained. If the ratio of lead titanate to a lead complex perovskite compound exceeds 33 mol %, the temperature dependence characteristics of dielectric constant and binding coefficient become conspicuous in the temperature range of room temperature to 70° C. That is, the electrical characteristics of the lead complex perovskite compound become unstable in the temperature range of room temperature to 70° C.

If the ratio of lead magnesium niobate to a lead complex perovskite compound is less than 24 mol %, a necessary dielectric constant cannot be obtained. If the ratio of lead titanate to a lead complex perovskite compound exceeds 74 mol %, the temperature dependence characteristics of dielectric constant and binding coefficient become conspicuous in the temperature range of room temperature to 70° C. That is, the electrical characteristics of the lead complex perovskite compound become unstable in the temperature range of room temperature to 70° C. If the ratio of lead indium niobate to a lead complex perovskite compound exceeds 50 mol %, it becomes difficult to prepare a single crystal of a lead complex perovskite compound. In addition, it is sometime impossible to obtain a single crystal of a lead complex perovskite compound composed of three highly homogeneous components (lead indium niobate, lead magnesium niobate, and lead titanate).

For the above reasons, in order to maintain a high dielectric constant and binding coefficient and reduce the above temperature dependence characteristics at room temperature to 70° C., a lead complex perovskite compound contains 0 mol % or more and 50 mol % or less of lead indium niobate, 24 mol % or more and 74 mol % or less of lead magnesium niobate, and 26 mol % or more and 33 mol % or less of lead titanate, and the sum of mol % of lead indium niobate and lead magnesium niobate is 67 mol % or more and 74 mol % or less, thus totaling to 100 mol %.

The piezoelectric single crystal may further contain 15 mol % or less of lead zirconate. In this case, the piezoelectric single crystal has the following composition. That is, this crystal contains 0 mol % or more and 15 mol % or less of lead zirconate, 0 mol % or more and 50 mol % or less of lead indium niobate, 0 mol % or more and 74 mol % or less of lead magnesium niobate, and 26 mol % or more and 33 mol % or less of lead titanate, thus totaling to 100 mol %. That is, when the crystal contains v mol % of lead zirconate, z mol % of lead indium niobate, y mol % of lead magnesium niobate, and x mol % of lead titanate, v=0 or more and 0.15 or less, x=0.26 or more and 0.33 or less, y=0.24 or more and 0.74 or less, z=0 or more and 0.5 or less, v+y+z=0.67 or more and 0.74 or less, and v+z+y+z 1.

Piezoelectric single crystals with the crystal orientations of all the planes being [100] are mainly used for an ultrasonic probe. In addition, small amounts of manganese oxide and the like may be added to these piezoelectric single crystals.

In order to set the operating center frequency of an ultrasonic probe to 2 MHz or more and 10 MHz or less, each piezoelectric transducer of the ultrasonic probes used for a medical ultrasonic diagnostic apparatus and an ultrasonic image examination apparatus has a thickness of, for example, 0.05 mm or more and 0.5 mm or less. The distance between the electrodes is 0.05 mm or more and 0.5 mm or less. In other words, the interval of the surfaces of one pair of electrodes which face the piezoelectric transducer is 0.05 mm or more and 0.5 mm or less.

A plurality of wafers (to be referred to as single crystal wafers hereinafter), each having a thickness of 0.1 mm or more and 0.7 mm or less, are prepared from near the middle portion of the single crystal ingot prepared by the above method by using a diamond blade or wire saw having a thickness of 0.1 mm or more and 0.5 mm or less. All the planes of each single crystal wafer have crystal orientation [100]. Subsequently, crystal plates (single crystal wafers), each having a thickness of, for example, 0.05 mm or more and 0.5 mm or less, whose planes having electrodes prepared thereon have crystal orientation [100], are prepared by lapping or polishing (step Sa2).

Subsequently, as electrodes, baked silver or gold or gold, platinum, nickel, or the like prepared by a sputtering method or plating method is formed on the front and rear surfaces of each single crystal wafer to a thickness of, for example, about 100 nm or more and 5,000 nm or less (step Sa3). The electrode provided on the front surface of the single crystal wafer will be referred to as the front-surface electrode, and the electrode provided on the rear surface of the single crystal wafer will be referred to as the rear-surface electrode. When providing electrodes by the sputtering method, deposition method, or plating method, in order to improve the adhesion property with respect to the single crystal wafer, it is preferable to form, as an underlying electrode, for example, a chromium (Cr), nickel (Ni), titanium (Ti), or palladium (Pd) electrode to a thickness of 10 nm or more and 100 nm or less. A single crystal wafer provided with electrodes will be referred to as a piezoelectric transducer hereinafter.

The following AC polarization process (step Sa4) is executed for this unpolarized piezoelectric transducer.

A polarization electric field in the AC polarization process (step Sa4) is an AC electric field with a sine or triangular waveform, which has a frequency of 0.1 Hz or more and 1,000 Hz or less without any offset (the absolute value of the maximum voltage is equal to the absolute value of the minimum voltage). A frequency of less than 0.1 Hz is a frequency with which the effects unique to this application (to be described later) are small. That is, in AC polarization with a frequency of less than 0.1 Hz, the rates of increase in dielectric constant and piezoelectric constant are 10% or less. In addition, a frequency exceeding 1,000 Hz tends to cause fine cracks in the single crystal wafer and to cause dielectric breakdown in the wafer due to the generation of heat. This makes the single crystal wafer breakable. For the above reasons, the frequency of an AC electric field needs to fall within the range of 0.1 Hz or more and 1,000 Hz or less. A peak-to-peak (to be referred to as pp hereinafter) electric field in this AC electric field is two times or more and six times or less a coercive electric field Ec of a piezoelectric transducer. With a pp electric field two times or less the coercive electric field, in AC polarization, the rates of increase in dielectric constant and piezoelectric constant are 10% or less. In addition, a pp electric field exceeding six times the coercive electric field tends to cause fine cracks in the single crystal wafer and to cause dielectric breakdown in the wafer due to the generation of heat. This makes the single crystal wafer breakable. For the above reasons, the pp electric field in AC polarization falls within the range of two times or more and six times or less the coercive electric field.

That is, the pp electric field is 0.5 kV/mm or more and 3.6 kV/mm or less. If the pp electric field is less than 0.5 kV/mm, it is difficult to obtain the shape characteristics and effects (to be described later) unique to this application. If the pp electric field exceeds 3.6 kV/mm, heat is generated in the single crystal wafer. This makes the single crystal wafer breakable.

For the above reasons, the pp electric field in an AC electric field preferably falls within the range of 0.8 kV/mm or more and 2 kV/mm or less. Assume that the process in which an AC electric field starts at 0 kV/mm and ends at 0 kV/mm through one wavelength (one period) is defined as one cycle. The polarization process (step Sa4) is the process of applying the above polarization signal to the single crystal wafer in the thickness direction through the prepared electrodes (the front-surface electrode and the rear-surface electrode) over two cycles or more and 1,000 cycles or less. If the number of cycles is less than two, it is difficult to obtain the shape characteristics and effects (to be described later) unique to this application. If the number of cycles exceeds 1,000, heat is generated in the single crystal wafer. This makes the single crystal wafer breakable. For the above reasons, the number of cycles of applying an AC electric field preferably falls within the range of two cycles or more and 1,000 cycles or less. Note that the number of times (cycles) of application of an AC electric field may be determined in accordance with single crystal materials. Note that in order to maintain a polarization state, the AC polarization process (step Sa4) is preferably executed in a predetermined temperature environment at a temperature (for example, room temperature) less than the phase transition temperatures (Trt, Trm, and Tmt). That is, at a temperature exceeding the phase transition temperature, polarization reversal occurs or piezoelectricity deteriorates. In order to prevent this, it is necessary to execute an AC polarization process at a temperature lower than the phase transition temperature.

The main purpose of DC polarization after AC polarization and a cutting process (to be described later) is to recover (align) variations in polarization caused by the heat generated in the single crystal wafer by the cutting process. For this reason, for example, the electric field used for DC polarization can be an electric field which is lower than a pp electric field in AC polarization and can recover variations in polarization. More specifically, an electric field used for DC polarization is 0.25 kV/mm or more and 2.5 kV/mm or less. The reason why a DC electric field is set to 0.25 kV/mm or more is that an electric field equal to or less than this value cannot implement sufficient polarization in the temperature range of room temperature to 100° C., and cannot obtain a sufficient dielectric constant and piezoelectric constant. In addition, the reason why an electric field is set to 2.5 kV/mm or less is that an electric field exceeding this value tends to cause dielectric breakdown at the time of polarization. Note that an electric field in DC polarization may be set to 0.5 kV/mm or more and 1.2 kV/mm or less. This is because an electric field in this range can easily implement polarization at a temperature between room temperature and 100° C., and can obtain a high dielectric constant and piezoelectric constant, with almost no dielectric breakdown. The application of a DC electric field after the above AC polarization can also be applied to Examples 1 to 31. In addition, the period of time during which DC polarization is executed depends on the amount of heat generated in a single crystal wafer by cutting or dicing. For example, this period of time is generally 1 sec or more and 30 min or less at room temperature (20° C. or higher and 25° C. or lower).

After the AC polarization process (step Sa4), a process using a DC electric field may be executed by using the same electrodes as those used in the AC polarization process (step Sa5). Note that the DC polarization process in step Sa5 may be executed immediately before the AC polarization process in step Sa4. In a DC polarization process, a DC electric field preferably falls within the range of 0.25 kV/mm or more and 2.5 kV/mm or less. In addition, the time intervals at which a DC electric field is applied are 1 sec or more and 30 min or less. Note that the DC electric field is lower than the pp electric field.

The following is a description of how diffraction X-ray measurement based on the Miller index (400) near 98° or higher and 102° C. or lower is performed on an unpolarized or depolarized single crystal wafer and a polarized single crystal wafer under the above X-ray diffraction conditions. Assume that the diffraction angle 2θ corresponding to the Miller index (400) when an X-ray diffraction experiment was conducted on an unpolarized single crystal wafer is defined as a first diffraction angle C. The FWHM of an X-ray intensity distribution corresponding to the first diffraction angle C is defined as a first FWHM W. Note that a depolarized single crystal wafer may be used instead of an unpolarized single crystal wafer.

Assume that the diffraction angle 2θ corresponding to the Miller index (400) when an X-ray diffraction experiment was conducted on a polarized single crystal wafer is defined as a second diffraction angle C2. The FWHM of an X-ray intensity distribution corresponding to the second diffraction angle C2 is defined as a second FWHM W2. The second FWHM W2 is 0.1° or more and 0.2° or less. The ratio (to be referred to as the FWHM ratio (W2/W) hereinafter) of the second FWHM to the first FWHM is, for example, 0.22 or more and 0.4 or less. In addition, the ratio (to be referred to as the diffraction angle ratio (C2/C) hereinafter) of the second diffraction angle C2 to the first diffraction angle C is not less than 1.0005 and not more than 1.005. That is, the ratio of the second FWHM W2 of diffracted X-rays based on the Miller index (400) of the single crystal piezoelectric body to the first FWHM W of diffracted X-rays based on the Miller index (400) of the unpolarized or depolarized single crystal piezoelectric body is 0.22 or more and 0.4 or less. In addition, the ratio of the second diffraction angle C2 at which diffracted X-rays based on the Miller index (400) of the single crystal piezoelectric body reaches a peak to the first diffraction angle C at which diffracted X-rays based on the Miller index (400) of the unpolarized or depolarized single crystal piezoelectric body reaches a peak is 1.0005 or more and 1.005 or less. A diffraction angle ratio and an FWHM ratio can be obtained by obtaining the second diffraction angle C2 and the second FWHM W2 by conducting an X-ray diffraction experiment on a polarized single crystal piezoelectric body and then obtaining the first diffraction angle C and the first FWHM W1 by conducting an X-ray diffraction experiment upon depolarizing the single crystal piezoelectric body.

Note that it can be checked by, for example, the following method whether a single crystal piezoelectric body is in a polarized state or unpolarized or depolarized state. That is, a current is applied to the single crystal piezoelectric body while the frequency is changed. When the single crystal piezoelectric body is in an unpolarized or depolarized state, no resonance occurs like an insulator, whereas when it in a polarized state, resonance occurs at a given frequency.

Note that the piezoelectric constant d33 was measured at 25° C. by using Berlincourt type Piezo d33 Meter, ZJ-3D, Institute of Acoustic of Academia Sinica. A dielectric constant and dielectric loss were measured at 1 kHz, 1 vrms, and 25° C. by using HP 4284A Precision LCR meter.

Examples 1 to 7

Figure 4:
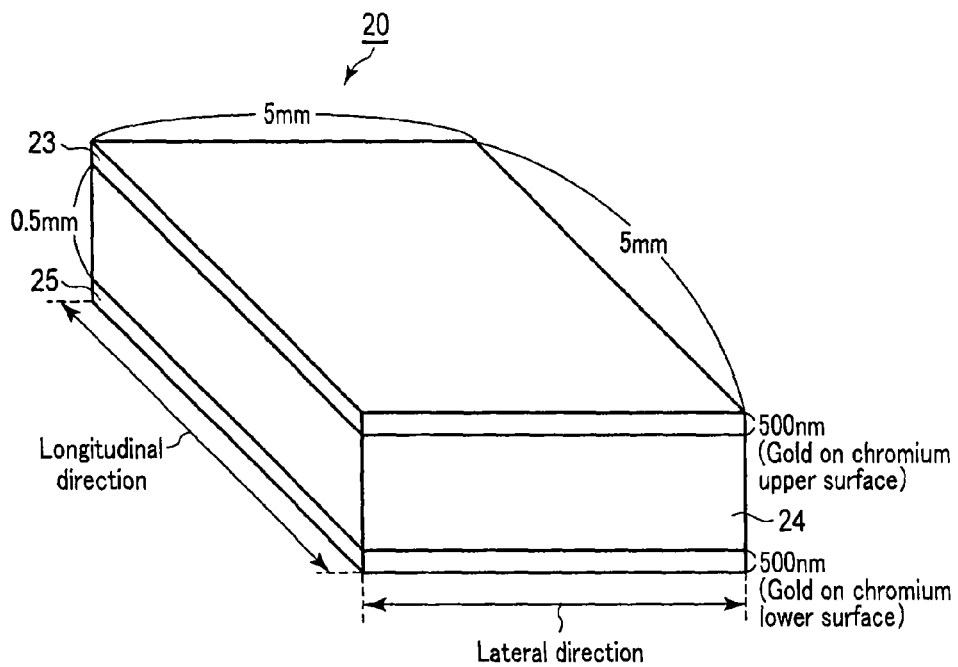
FIG. 4 is a perspective view showing an example of the outer appearance of a piezoelectric transducer according to Examples 1 to 7 of this embodiment.

A [100] plate of a $0.71Pb(Mg_{1/3}, Nb_{2/3})O_3$-$0.29PbTiO_3$ (PMN-PT 71/29) single crystal 24 of lead magnesium niobate-lead titanate $(Pb(Mg_{1/3}, Nb_{2/3})O_3$—$PbTiO_3$ is polished to have outer dimensions of 12 mm×12 mm and a thickness of 0.5 mm. Thereafter, chromium (Cr) is deposited as a front-surface electrode 23 and a rear-surface electrode 25 on the upper and lower surfaces of the [100] plate (12 mm×12 mm) to a thickness of 20 nm by a sputtering apparatus. Gold is deposited on the chromium film to a thickness of 300 nm by the sputtering apparatus. The [100] plate of the single crystal provided with the electrodes 23 and 25 described above is then cut by a dicer to prepare a piezoelectric transducer 20 having a longitudinal/lateral length of 5 mm and a thickness of 0.5 mm. FIG. 4 shows an example of the piezoelectric transducer 20 having a longitudinal/lateral length of 5 mm and a thickness of 0.5 mm. The phase transition temperature Trt of this piezoelectric transducer is about 100° C. A Curie temperature Tc is 140° C. The coercive electric field Ec measured by a Sawyer-Tower circuitry was 0.25 kV/mm at room temperature. An AC electric field with a triangular waveform which has a frequency of 0.1 Hz and a peak-to-peak (pp) value of 0.2 kV/mm or more and 3 kV/mm or less was applied 20 times between the electrodes of this piezoelectric transducer. A DC electric field of 0.5 kV/mm is applied between the same electrodes over 5 min at room temperature before and after the application of the AC electric field. An AC electric field may be applied after the DC electric field is applied in this manner.

Figure 5:
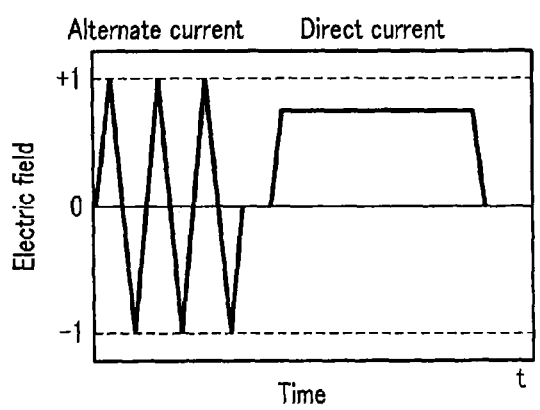
FIG. 5 is a graph showing an example of an AC electric field and DC electric field which are applied to a piezoelectric transducer according to this embodiment.
Figure 6:
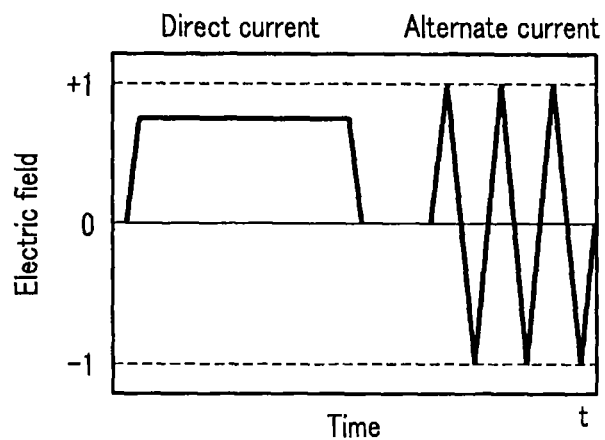
FIG. 6 is a graph showing an example of an AC electric field and DC electric field which are applied to a piezoelectric transducer according to this embodiment.

FIG. 5 is a graph showing an example of how a DC electric field is applied after the application of an AC electric field. Referring to FIG. 5, the pp values are normalized to ±1. FIG. 6 is a graph showing an example of how an AC electric field is applied after the application of a DC electric field.

A room temperature dielectric constant, a dielectric loss DF (%), and the piezoelectric constant d33 (pC/N) were measured 24 hr after a polarization process. In addition, the second diffraction angle C2, the second FWHM W2, and the peak value of X-ray intensities concerning the second diffraction angle were obtained based on X-ray diffraction angle measurement results concerning the Miller index (400) of a prepared piezoelectric transducer. In addition, characteristics such as the first diffraction angle C and the first FWHM W were measured on a piezoelectric transducer before polarization or depolarized piezoelectric transducer by executing X-ray diffraction.

Figure 7:
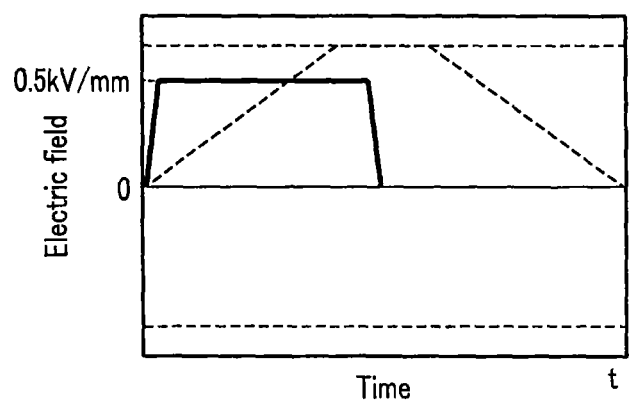
FIG. 7 is a graph showing an example of the application of a DC electric field according to a reference example.

Tables 1 and 2 show various types of characteristics of piezoelectric transducers polarized by the application of AC electric fields, together with various characteristics of PMNT 71/29 piezoelectric transducers having the same shape to which no AC electric field has been applied. Note that the values in the tables are average values obtained from four samples in the respective cases. FIG. 7 is a graph showing an example of the application of a DC electric field according to Reference Example 4.

TABLE 1

| Example/ Reference Example | Alternate Current (AC) Process Condition PP voltage | Room Dielectric Constant | Dielectric Loss DF(%) | Piezoelectric Constant d33(pC/N) |
|---|---|---|---|---|
| Example 1 | 0.5 kV/mm AC | 6380 | 0.53 | 2170 |
| Example 1 | 0.8 kV/mm AC | 7420 | 0.52 | 2490 |
| Example 3 | 1.0 kV/mm AC | 8550 | 0.45 | 2800 |
| Example 4 | 1.5 kV/mm AC | 7920 | 0.45 | 2650 |
| Example 5 | 2.0 kV/mm AC | 7430 | 0.48 | 2350 |
| Example 6 | 2.5 kV/mm AC | 7000 | 0.48 | 2100 |
| Example 7 | 3.0 kV/mm AC | 6200 | 0.498 | 2050 |
| Reference Example 1 | None (Unpolarized) | 2800 | 2.0 | — |
| Reference Example 2 | 0.2 kV/mm AC | 5500 | 0.69 | 1560 |
| Reference Example 3 | 5.0 kV/mm AC | Dielectric breakdown | | |
| Reference Example 4 | No AC Process. DC, 0.5 kV/mm, 5 min | 5500 | 0.70 | 1570 |

TABLE 2

| Process Condition PP Voltage | Example/ Reference Example | (400) Diffraction Angle 2θ (deg) | FWHM (W) (deg) | Peak Value | W2/W | C2/C |
|---|---|---|---|---|---|---|
| 0.5 kV/mm AC | Example 1 | 99.998 | 0.155 | 8600 | 0.388 | 1.00051 |
| 0.8 kV/mm AC | Example 2 | 100.002 | 0.14 | 9000 | 0.35 | 1.00055 |
| 1 kV/mm AC | Example 3 | 100.009 | 0.14 | 9500 | 0.35 | 1.00062 |
| 1.5 kV/mm AC | Example 4 | 100.013 | 0.13 | 9948 | 0.325 | 1.00066 |
| 2 kV/mm AC | Example 5 | 100.015 | 0.125 | 9990 | 0.3125 | 1.00068 |
| 2.5 kV/mm AC | Example 6 | 100.001 | 0.13 | 9870 | 0.325 | 1.00054 |
| 3 kV/mm AC | Example 7 | 99.995 | 0.14 | 9900 | 0.35 | 1.00048 |
| Unpolarization | Reference Example 1 | 99.947 | 0.4 | 3100 | 1 | 1 |
| 0.2 kV/mm AC | Reference Example 2 | 99.955 | 0.29 | 5000 | 0.725 | 1.00008 |
| 5 kV/mm AC | Reference Example 3 | Dielectric breakdown | | | | |
| DC polarization 0.5 kV/mm | Reference Example 4 | 99.942 | 0.2 | 8099 | 0.475 | 0.99995 |

As is obvious from Tables 1 and 2, the samples (Examples 1 to 7) obtained by the application of pp electric fields two times or more and six times or less the coercive electric field Ec, i.e., AC electric fields of 0.5 kV/mm or more and 3.0 kV/mm or less, before the application of DC electric fields exhibited increases in dielectric constant and piezoelectric constant in the range of 30% or more and 80% or less as compared with Reference Examples 1 to 4 obtained without the application of AC electric fields. In addition, these samples exhibited slight reductions in dielectric loss. Furthermore, the FWHM ratios (W2/W) of these materials are 0.32 or more and 0.39 or less, and exhibit improvements in crystallinity by AC polarization. Moreover, the diffraction angle ratios (C2/C) are 1.0005 or more and 1.0008 or less. That is, the c-axis lattice spacings have decreased.

Figure 8:
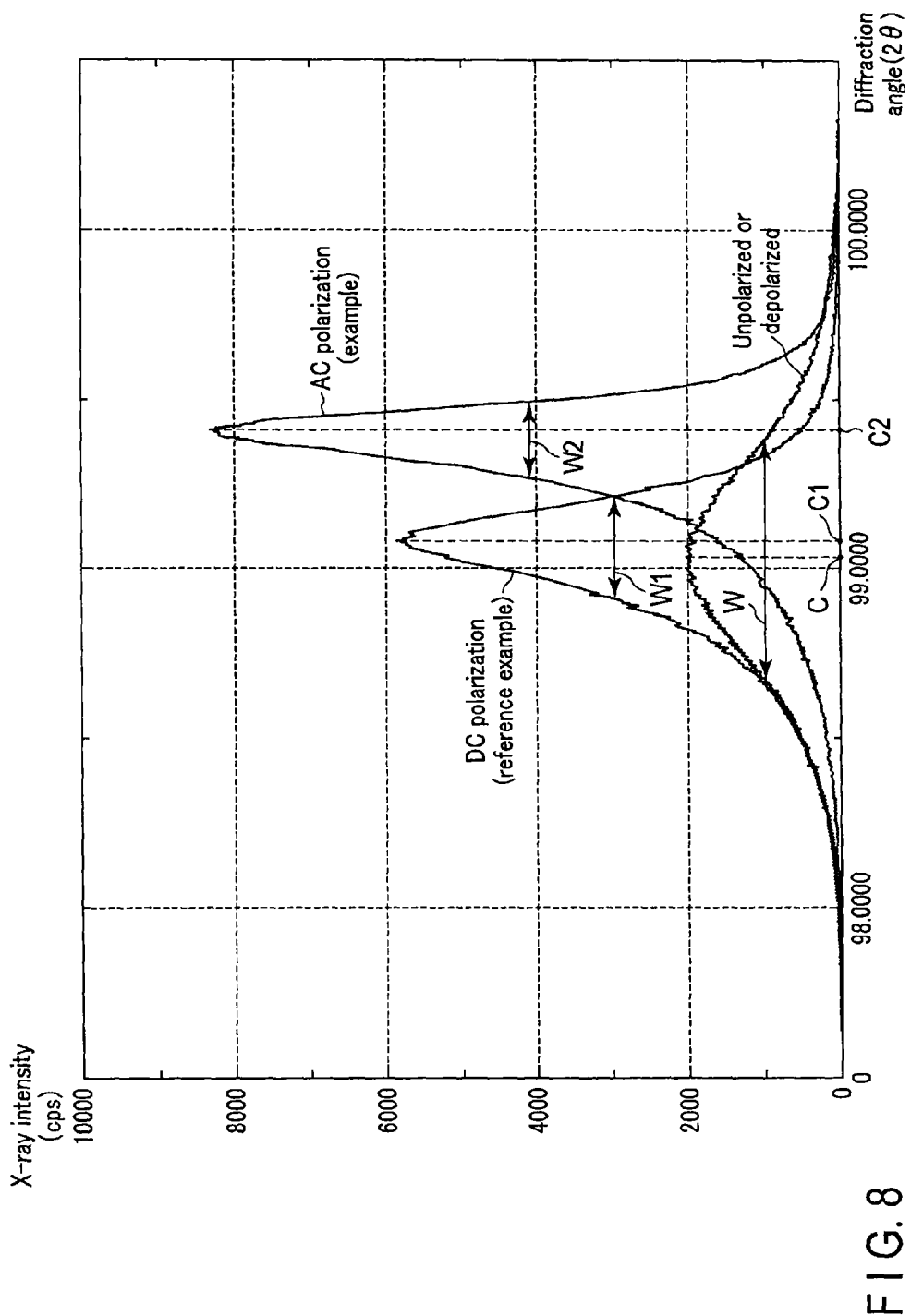
FIG. 8 is a graph showing an example of an X-ray intensity distribution with respect to diffraction angles (2θ) on X-ray diffraction results concerning the Miller index (400) according to this embodiment.

FIG. 8 a graph showing an example of X-ray intensity distributions with respect to diffraction angles (λθ) on. X-ray diffraction results concerning the Miller index (400) according to an unpolarized or depolarized piezoelectric transducer, each reference example, and each example. Referring to FIG. 8, the abscissa of the graph represents the diffraction angles (2θ). The ordinate in FIG. 8 represents the X-ray intensities (count/sec). The diffraction angle C2 corresponding to the peak value of the X-ray intensities of each example is larger than the diffraction angle C1 corresponding to the peak value of the X-ray intensities of each reference example, and the diffraction angle C corresponding to the peak value of the X-ray intensities of the unpolarized or depolarized piezoelectric transducer. That is, it is obvious that the c-axis lattice spacing in each example has decreased as compared with the unpolarized or depolarized piezoelectric transducer and each reference example. In addition, the FWHM W2 corresponding to the diffraction angle C2 is smaller than the FWHM W1 corresponding to the diffraction angle C1 and the FWHM W corresponding to the diffraction angle C. That is, each example obviously exhibits an improvement crystallinity as compared with the unpolarized or depolarized piezoelectric transducer and each reference example.

Examples 8 to 14

A [100] plate of a $0.24Pb(In_{1/2}Nb_{1/2})O_3$-$0.45Pb(Mg_{1/3}Nb_{2/3})$-$0.31PbTiO_3$ (PIMNT 24/45/31) single crystal of lead indium niobate-lead magnesium niobate-lead titanate ($Pb(In_{1/2}Nb_{1/2})O_3$—$Pb(Mg_{1/3}Nb_{2/3})O_3$—$PbTiO_3$) is polished to have outer dimensions of 12 mm×12 mm and a thickness of 0.3 mm. Thereafter, palladium (Pd) strike plating is performed on the upper and lower surfaces of the [100] plate (12 mm×12 mm) by using a wet electroless plating method. Thereafter, nickel (Ni) is deposited on the upper surface of the palladium film to a thickness of 500 nm. Subsequently, gold (Au) is deposited on the upper surface of the nickel film to a thickness of 200 nm. The [100] plate of the single crystal provided with the electrodes described above is then cut by a dicer to prepare a piezoelectric transducer having a longitudinal/lateral length of 5 mm and a thickness of 0.5 mm. The phase transition temperature Trt of this piezoelectric transducer is about 100° C. A Curie temperature Tc is 190° C. The coercive electric field Ec measured by a Sawyer-Tower circuitry was 0.6 kV/mm at room temperature. An AC electric field with a sine waveform which has a frequency of 50 Hz and a peak-to-peak (pp) value of 0.3 kV/mm or more and 3 kV/mm or less was applied 50 times between the electrodes of this piezoelectric transducer. A DC electric field of 0.8 kV/mm is applied between the same electrodes over 5 min at room temperature before and after the application of the AC electric field.

A room temperature dielectric constant, the dielectric loss DF (%), and the piezoelectric constant d33 (pC/N) were measured 24 hr after a polarization process. In addition, the second diffraction angle C2, the second FWHM W2, and the peak value of X-ray intensities concerning the second diffraction angle were obtained based on X-ray diffraction measurement results concerning the Miller index (400) of each prepared piezoelectric transducer. In addition, characteristics such as the first diffraction angle C and the first FWHM W were measured on a piezoelectric transducer before polarization or depolarized piezoelectric transducer by executing X-ray diffraction.

Tables 3 and 4 show various types of characteristics of piezoelectric transducers polarized by the application of AC electric fields, together with various characteristics of PIMNT 24/45/31 piezoelectric transducers having the same shape to which no AC electric field has been applied. Note that the values in the tables are average values obtained from four samples in the respective cases.

TABLE 3

| Example/ Reference Example | Alternate Current (AC) Process Condition | Room Dielectric Constant | Dielectric Loss DF(%) | Piezoelectric Constant d33(pC/N) |
|---|---|---|---|---|
| Example 8 | 1.2 kV/mm AC | 7580 | 0.72 | 2280 |
| Example 9 | 1.5 kV/mm AC | 8300 | 0.76 | 2850 |
| Example 10 | 1.8 kV/mm AC | 8800 | 0.52 | 3200 |
| Example 11 | 2.0 kV/mm AC | 9800 | 0.55 | 3850 |
| Example 12 | 2.5 kV/mm AC | 8950 | 0.55 | 3240 |
| Example 13 | 3.0 kV/mm AC | 7700 | 0.50 | 2280 |
| Example 14 | 3.5 kV/mm AC | 7500 | 0.65 | 2200 |
| Reference Example 5 | None (Unpolarized) | 2350 | 3.0 | — |
| Reference Example 6 | 0.6 kV AC | 6500 | 0.98 | 1980 |
| Reference Example 7 | 5.0 kV/mm AC | Dielectric breakdown | — | — |
| Reference Example 8 | No AC Process. DC, 0.5 kV/mm, 5 min | 6500 | 0.98 | 1950 |

TABLE 4

| Process Condition PP Voltage | Example/ Reference Example | (400) Diffraction Angle 2θ (deg) | FWHM (W) (deg) | Peak Value | W2/W | C2/C |
|---|---|---|---|---|---|---|
| 1.2 kV/mm AC | Example 8 | 99.299 | 0.22 | 9600 | 0.330 | 1.000504 |
| 1.5 kV/mm AC | Example 9 | 99.305 | 0.17 | 9920 | 0.255 | 1.000564 |
| 1.8 kV/mm AC | Example 10 | 99.315 | 0.155 | 9800 | 0.233 | 1.000665 |
| 2.0 kV/mm AC | Example 11 | 99.324 | 0.164 | 10020 | 0.246 | 1.000756 |
| 2.5 kV/mm AC | Example 12 | 99.329 | 0.162 | 10050 | 0.243 | 1.000806 |

TABLE 4-continued

| Process Condition PP Voltage | Example/ Reference Example | (400) Diffraction Angle 2θ (deg) | FWHM (W) (deg) | Peak Value | W2/W | C2/C |
|---|---|---|---|---|---|---|
| 3 kV/mm AC | Example 13 | 99.299 | 0.169 | 10000 | 0.254 | 1.000504 |
| 3.5 kV/mm AC | Example 14 | 99.299 | 0.24 | 9910 | 0.360 | 1.000504 |
| Unpolarization | Reference Example 5 | 99.249 | 0.666 | 1180 | 1 | 1 |
| 0.5 kV/mm AC | Reference Example 6 | 99.249 | 0.29 | 5000 | 0.435 | 1 |
| 5 kV/mm AC | Reference Example 7 | Dielectric breakdown | | | | |
| DC polarization 1.8 kV/mm | Reference Example 8 | 99.239 | 0.285 | 5374 | 0.428 | 0.999899 |

As is obvious from Tables 3 and 4, the samples (Examples 8 to 14) obtained by the application of pp electric fields two times or more and six times or less the coercive electric field Ec, i.e., AC electric fields of 1.2 kV/mm or more and 3.5 kV/mm or less, before the application of DC electric fields exhibited increases in dielectric constant in the range of 15% or more and 51% or less and increases in piezoelectric constant in the range of 13% or more and 97% or less as compared with Reference Examples 5 to 8 obtained without the application of AC electric fields. In addition, these samples exhibited slight reductions in dielectric loss. Furthermore, the FWHM ratios (W2/W) of these materials are 0.23 or more and 0.36 or less, and exhibit improvements in crystallinity by AC polarization. Moreover, the diffraction angle ratios (C2/C) are 1.0005 or more and 1.0008 or less. That is, the c-axis lattice spacings have decreased.

Figure 9:
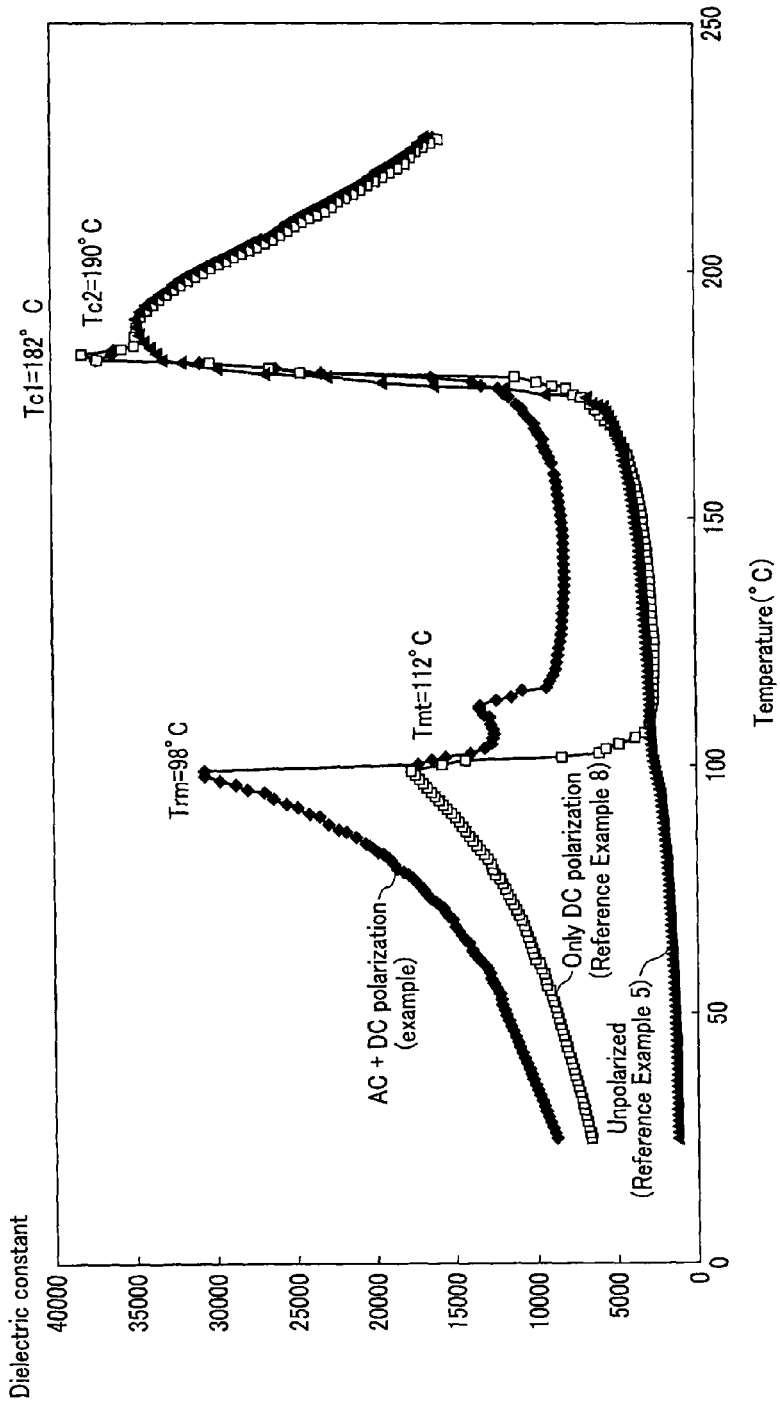
FIG. 9 is a graph showing the temperature characteristic of the dielectric constant of a piezoelectric transducer according to this embodiment, together with the temperature characteristics of the dielectric constants of a DC-polarized piezoelectric transducer and unpolarized piezoelectric transducer.

FIG. 9 is a graph showing an example of the dielectric constant temperature characteristics respectively obtained by applying no polarization, DC polarization, and DC/AC polarization to PIMNT 24/45/31 single crystals according to the examples. As shown in FIG. 9, the phase transition temperature (Trm) of each example is between 80° C. or more and 150° C. or less. As is obvious from FIG. 9, the dielectric constants at lower than the Curie temperature (Tc) in each example are larger than those of PIMNT 24/45/31 for which conventional DC polarization has been executed.

Examples 15 to 21

A [100] plate of a 0.56Pb(Mg$_{1/3}$Nb$_{2/3}$)O$_3$-0.32PbTiO$_3$-0.12PbZrO$_3$ (PMNZT 56/32/12) single crystal of lead magnesium niobate-lead titanate-lead zirconate (Pb(Mg$_{1/3}$Nb$_{2/3}$)O$_3$—PbTiO$_3$—PbZrO$_3$) is prepared by solid state crystal growth. Thereafter, titanium (Ti) is deposited on the upper and lower surfaces of the [100] plate to a thickness of 20 nm. Subsequently, gold (Au) is deposited on the titanium film to a thickness of 300 nm. The [100] plate of the single crystal provided with the electrodes described above is then cut by a dicer to prepare four piezoelectric transducers each having a longitudinal/lateral length of 5 mm and a thickness of 0.5 mm. The phase transition temperature Trt of each piezoelectric transducer is about 115° C. The Curie temperature Tc is 185° C. The coercive electric field Ec measured by a Sawyer-Tower circuitry was 0.5 kV/mm at room temperature. A DC electric field of 1.5 kV/mm was applied between the electrodes of this piezoelectric transducer over 10 min. An AC electric field with a sine waveform which has a frequency of 10 Hz and a pp value of 0.3 kV/mm or more and 3 kV/mm or less was applied between the same electrodes over 20 cycles.

Various types of characteristics such as a room temperature dielectric constant, the dielectric loss DF (%), the piezoelectric constant d33 (pC/N), the second diffraction angle C2, the second FWHM W2, and the peak height of the second diffraction angle were measured 24 hr after a polarization process. In addition, characteristics such as the first diffraction angle C and the first FWHM W were measured by executing X-ray diffraction with respect to a piezoelectric transducer before polarization or depolarized piezoelectric transducer.

Tables 5 and 6 show various types of characteristics of piezoelectric transducers polarized by the application of AC electric fields, together with various characteristics of PMNZT 56/32/12 piezoelectric transducers having the same shape to which no AC electric field has been applied. Note that the values in the tables are average values obtained from four samples in the respective cases.

TABLE 5

| Example/ Reference Example | Alternate Current (AC) Process Condition | Room Dielectric Constant | Dielectric Loss DF(%) | Piezoelectric Constant d33(pC/N) |
|---|---|---|---|---|
| Example 15 | 1.0 kV/mm AC | 6180 | 0.82 | 1730 |
| Example 16 | 1.5 kV/mm AC | 6800 | 0.81 | 2090 |
| Example 17 | 1.8 kV/mm AC | 7350 | 0.80 | 2290 |
| Example 18 | 2.0 kV/mm AC | 7730 | 0.75 | 2600 |
| Example 19 | 2.0 kV/mm AC | 6950 | 0.69 | 2180 |
| Example 20 | 2.5 kV/mm AC | 6980 | 0.68 | 1880 |
| Example 21 | 3.0 kV/mm AC | 6210 | 0.78 | 1750 |
| Reference Example 9 | None (Unpolarized) | 2300 | 2.5 | — |
| Reference Example 10 | 0.5 kV AC | 5160 | 0.98 | 1500 |
| Reference Example 11 | 5.0 kV/mm AC | Dielectric breakdown | — | — |
| Reference Example 12 | No AC Process. DC, 0.5 kV/mm, 5 min | 5150 | 0.98 | 1480 |

TABLE 6

| Process Condition PP Voltage | Example/ Reference Example | (400) Diffraction Angle 2θ (deg) | FWHM (W) (deg) | Peak Value | W2/W | C2/C |
|---|---|---|---|---|---|---|
| 1.0 kV/mm AC | Example 15 | 99.7 | 0.22 | 12000 | 0.316 | 1.001034 |
| 1.5 kV/mm AC | Example 16 | 99.7 | 0.17 | 13500 | 0.244 | 1.001034 |
| 1.8 kV/mm AC | Example 17 | 99.7 | 0.155 | 15500 | 0.222 | 1.001034 |
| 2.0 kV/mm AC | Example 18 | 99.731 | 0.167 | 17000 | 0.240 | 1.001345 |
| 2.5 kV/mm AC | Example 19 | 99.7 | 0.162 | 15000 | 0.232 | 1.001034 |
| 3 kV/mm AC | Example 20 | 99.7 | 0.169 | 14200 | 0.242 | 1.001034 |
| 3.5 kV/mm AC | Example 21 | 99.7 | 0.23 | 15000 | 0.330 | 1.001034 |
| Unpolarization | Reference Example 9 | 99.597 | 0.697 | 1530 | 1 | 1 |
| 0.5 kV/mm AC | Reference Example 10 | 99.249 | 0.29 | 8000 | 0.416 | 1 |
| 5 kV/mm AC | Reference Example 11 | Dielectric breakdown | | | | |
| DC polarization 1.8 kV/mm | Reference Example 12 | 99.615 | 0.29 | 9470 | 0.416 | 1.000181 |

As is obvious from Tables 5 and 6, the samples (Examples 15 to 21) obtained by the application of pp electric fields as AC electric fields of 1 kV/mm or more and 3.5 kV/mm or less before the application of DC electric fields exhibited increases in dielectric constant in the range of 20% or more and 50% or less and increases in piezoelectric constant in the range of 16% or more and 75% or less as compared with Reference Examples 9 to 12 obtained without the application of AC electric fields. In addition, these samples exhibited reductions in dielectric loss. Furthermore, the FWHM ratios (W2/W) of these materials are 0.22 or more and 0.33 or less, and exhibit improvements in crystallinity by AC polarization. Moreover, the diffraction angle ratios (C2/C) are 1.0001 or more and 1.0002 or less. That is, the c-axis lattice spacings have decreased.

Examples 22 to 30

A [100] plate of a 0.71Pb(Mg$_{1/3}$Nb$_{2/3}$)O$_3$-0.29PbTiO$_3$ (PMNT 71/29) single crystal of lead magnesium niobate-lead titanate (Pb(Mg$_{1/3}$Nb$_{2/3}$)O$_3$—PbTiO$_3$ is polished to have outer dimensions of 12 mm×12 mm and a thickness of 0.05 mm or more and 2.0 mm or less. Thereafter, gold is deposited on the upper and lower surfaces of the [100] plate (12 mm×12 mm) to a thickness of 300 nm by a deposition apparatus. The electrodes on the upper and lower surface sides will be referred to as the first and second electrodes, respectively. The [100] plate of the single crystal provided with the electrodes described above is then cut by a dicer to prepare a plurality of piezoelectric transducers having a longitudinal/lateral length of 5 mm and different thicknesses of 0.5 mm or more and 2.0 mm or less. AC electric fields with triangular waveforms which have frequencies of 0.1 Hz to 2,000 Hz and a pp value of 0.8 kV/mm are applied between the electrodes of the plurality of prepared piezoelectric transducers at temperatures of 25° C., 80° C., and 120° C. over 0.1 min or more and 30 min or less, respectively. A DC electric field of 0.5 kV/mm is applied between the same electrodes over 10 min at room temperature after the application of the AC electric field. A room temperature dielectric constant, the dielectric loss DF (%), and the piezoelectric constant d33 (pC/N) were measured 24 hr after a polarization process.

Table 7 shown below indicates various characteristics of piezoelectric transducers polarized by the application of AC electric fields. Note that the values in the tables are average values obtained from four samples in the respective cases.

TABLE 7

| Example/ Reference Example | Thickness (mm) | AC Application Temperature (° C.) | AC Frequency (Hz) | AC Application Time (min) | Room Dielectric Constant | Dielectric Loss DF (%) | Piezoelectric Constant d33 (pC/N) |
|---|---|---|---|---|---|---|---|
| Example 22 | 0.05 | 25 | 0.1 | 5 | 5950 | 0.58 | 1880 |
| Example 23 | 0.1 | 25 | 0.1 | 5 | 6300 | 0.49 | 2010 |
| Example 24 | 0.2 | 25 | 1 | 0.5 | 8010 | 0.43 | 2240 |
| Example 25 | 0.4 | 25 | 1 | 0.5 | 8750 | 0.56 | 2650 |
| Example 26 | 0.5 | 25 | 10 | 0.5 | 8000 | 0.57 | 2430 |
| Example 27 | 0.3 | −10 | 1 | 0.1 | 6600 | 0.56 | 1820 |
| Example 28 | 0.3 | 60 | 1 | 1 | 7750 | 0.59 | 2360 |
| Example 29 | 0.3 | 80 | 50 | 0.1 | 7680 | 0.55 | 2210 |

TABLE 7-continued

| Example/Reference Example | Thickness (mm) | AC Application Temperature (° C.) | AC Frequency (Hz) | AC Application Time (min) | Room Dielectric Constant | Dielectric Loss DF (%) | Piezoelectric Constant d33 (pC/N) |
|---|---|---|---|---|---|---|---|
| Example 30 | 0.3 | 25 | 100 | 0.2 | 7000 | 0.48 | 2050 |
| Reference Example 10 | 0.8 | 25 | 1 | 0.05 | 5560 | 0.68 | 1530 |
| Reference Example 11 | 2.0 | 40 | 1 | 1 | 5410 | 0.68 | 1560 |
| Reference Example 12 | 0.3 | 60 | 10 | 30 | Dielectric breakdown | — | — |
| Reference Example 13 | 0.3 | 120 | 2000 | 2 | Dielectric breakdown | — | — |
| Reference Example 14 | 0.3 | 125 | 1 | 1 | 5420 | 0.68 | 1590 |

As is obvious from Table 7, the piezoelectric transducers having thicknesses (the distances between the first and second electrodes) of 0.5 mm or less exhibit noticeable improvements in dielectric constant and piezoelectric constant. In contrast to this, the piezoelectric transducers having thicknesses of 0.5 mm or more and 2.0 mm or less exhibit small improvements in dielectric constant and piezoelectric constant. In addition, when the AC frequency exceeds 100 Hz or the AC application time exceeds 10 min, improvements in dielectric constant and piezoelectric constant decrease, and dielectric breakdown tends to occur. Furthermore, as is obvious, when the temperature at AC application exceeds 100° C., the effect of improving dielectric/piezoelectric characteristics decreases.

Example 31

This example relates to an ultrasonic probe. FIG. 10 shows an example of the structure of the ultrasonic probe according to this example. The arrangement of an ultrasonic probe using the piezoelectric transducer prepared through the above polarization process will be described below with reference to FIG. 10.

As shown in FIG. 10, an ultrasonic probe 100 includes a backing member 102, a signal FPC (Flexible Printed Circuit) 104, a single crystal piezoelectric transducer element 106, a first acoustic matching layer 108, a second acoustic matching layer 110, a ground FPC 112, and an acoustic lens 114. For the sake of simplicity, FIG. 10 omits an illustration of the first and second acoustic matching layers and ground FPC on the front surface of a single crystal piezoelectric transducer element 1061.

The backing member 102 is made of rubber. A material having a low acoustic impedance (AI=2 MRayls or more and 6 MRayls or less) or a metal with high hardness is used for the backing member 102. The signal FPC 104 is provided on the front surface side of the backing member 102. Metal wirings are arranged on the front surface side of the signal FPC 104. The single crystal piezoelectric transducer element 106 is prepared by dicing the above piezoelectric transducer (a single crystal wafer provided with electrodes). The single crystal piezoelectric transducer element 106 includes a single crystal piezoelectric body formed from the lead complex perovskite compound described in Examples 1 to 30 and electrodes (a front-surface electrode (first electrode) and a rear-surface electrode (second electrode)) (not shown) on the ultrasonic wave emission surface side (first surface side) and rear surface side (second surface side) of the single crystal piezoelectric body. Note that an underlying electrode may be provided on the single crystal piezoelectric body side of each electrode. The first acoustic matching layer 108 is provided on the ultrasonic wave emission surface side of the single crystal piezoelectric transducer element 106. The first acoustic matching layer 108 includes electrodes (not shown) on the front surface side and the rear surface side. The second acoustic matching layer 110 is provided on the front surface side of the first acoustic matching layer 108. The second acoustic matching layer 110 includes electrodes (not shown) on the front surface side and the rear surface side.

The ground FPC 112 includes a ground electrode on the rear surface side. The ground FPC 112 is provided on the front surface side of the second acoustic matching layer 110. The third acoustic matching layer 111 is provided on the front surface side of the ground FPC 112. The acoustic lens 114 is provided on the front surface side of a third acoustic matching layer 111.

Note that two or four acoustic matching layers may be arranged on the ultrasonic wave emission surface side of the single crystal piezoelectric transducer element 106 in place of three acoustic matching layers. In this case, an acoustic matching layer may be formed on the ground FPC 112 or omitted.

When a plurality of acoustic matching layers are provided on the ultrasonic wave emission surface side of the single crystal piezoelectric transducer element 106, the acoustic impedances of the respective acoustic matching layers decrease stepwise from the single crystal piezoelectric transducer element 106 to the acoustic lens 114. For example, in the case of one acoustic matching layer, the first acoustic matching layer (first acoustic matching layer 108) immediately on the single crystal piezoelectric transducer element 106 has an acoustic impedance of 4 MRayls or more and 7 MRayls or less at 25° C. In this case, the first acoustic matching layer 108 is preferably formed from a material whose acoustic impedance has been adjusted by, for example, adding oxide particles to carbon as a conductive material and epoxy resin as an organic substance.

In the case of two acoustic matching layers, the first acoustic matching layer 108 immediately on the single crystal piezoelectric transducer element 106 is preferably formed from a material having an acoustic impedance of 5 MRalys or more and 10 MRalys or less at 25° C., and the second acoustic matching layer (second acoustic matching layer 110) is preferably formed from a material having an acoustic impedance of 2 MRalys or more and 4 MRalys or less. In this case, the first acoustic matching layer 108 is formed from, for example, carbon and an oxide-containing epoxy resin material. The second acoustic matching layer 110 is preferably formed from, for example, epoxy silicone or a polyethylene-based resin material. Note that when an insulating epoxy material is used for an acoustic matching layer, the surface of the acoustic matching layer may be provided with conductivity by plating or the like, as needed.

In the case of three acoustic matching layers, the first acoustic matching layer 108 is preferably formed from, for example, a glass material, the second acoustic matching layer 110 is preferably formed from, for example, a material obtained by filling carbon and epoxy with an oxide, and the third acoustic matching layer 111 is preferably formed from a polyethylene-based resin material. When an insulating material is used for an acoustic matching layer, the surface of the acoustic matching layer may be provided with conductivity by plating or the like, as needed.

Figure 11:
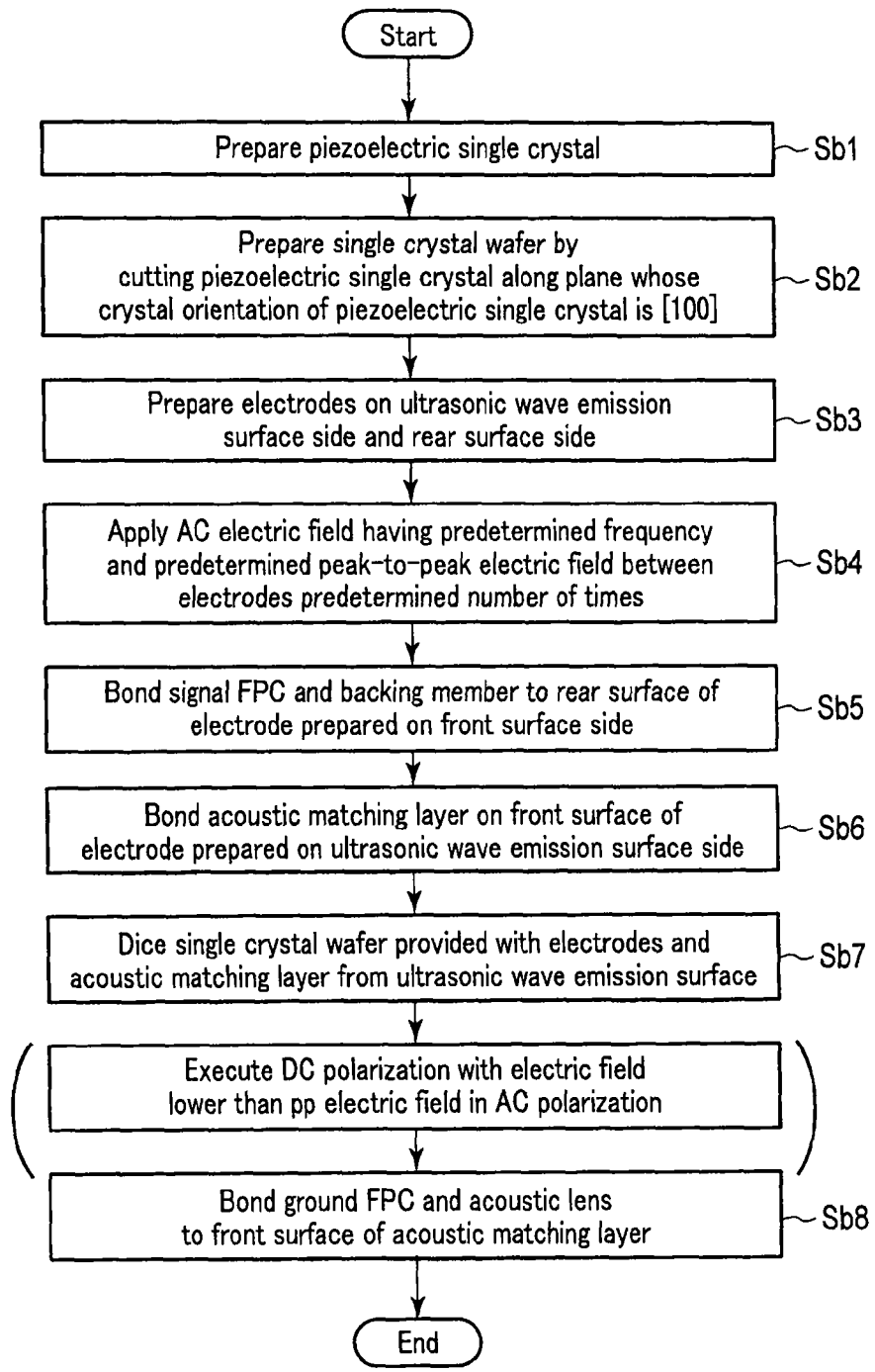
FIG. 11 is a flowchart showing a procedure for manufacturing an ultrasonic probe according to Example 4 of this embodiment.

FIG. 11 shows an example of a flowchart showing a procedure for manufacturing an ultrasonic probe according to this embodiment.

FIG. 11 is a flowchart showing a procedure for a method of manufacturing the ultrasonic probe 100 described with reference to FIG. 10. First of all, a piezoelectric transducer is prepared by the above piezoelectric transducer manufacturing method (step Sb1 to step Sb4). More specifically, a piezoelectric transducer is prepared as follows.

As a piezoelectric transducer of this ultrasonic probe, a $0.24Pb(In_{1/2}Nb_{1/2})O_3$-$0.45Pb(Mg_{1/3}Nb_{2/3})O_3$-$0.31PbTiO_3$ (PIMNT 24/45/31) single crystal of lead indium niobate-lead magnesium niobate-lead titanate ($Pb(In_{1/2}Nb_{1/2})O_3$—$Pb(Mg_{1/3}Nb_{2/3})O_3$—$PbTiO_3$) is prepared (step Sb1). A single crystal wafer is prepared by cutting the prepared piezoelectric single crystal along a plane whose crystal orientation is [100] (step Sb2). At this time, the single crystal wafer of the [100] plate is polished and shaped to have outer dimensions of 12 mm×26 mm and a thickness of 0.28 mm. Thereafter, NiCr is deposited on the upper surface (ultrasonic wave emission surface) and lower surface (rear surface) of the [100] plate (12 mm×26 mm) to a thickness of 10 nm by a sputtering apparatus. Likewise, gold is deposited on the NiCr films to a thickness of 300 nm by using the sputtering apparatus. With this process, electrodes are prepared on the ultrasonic wave emission surface side and rear surface side of the single crystal wafer (step Sb3). An AC electric field having a predetermined frequency (e.g., 1 Hz) and a predetermined pp value (e.g., 1.6 kV/mm) is applied between the prepared electrodes over 15 cycles (step Sb4).

A medical ultrasonic probe having a center frequency of about 3 MHz is manufactured by using the piezoelectric transducer to which the above AC polarization has been executed. The backing member 102 is prepared by mixing tungsten and zinc oxide fiber with epoxy resin. The density of the prepared backing member 102 is 2.5. The sound velocity of the prepared backing member 102 is 2,200 m/s. The acoustic impedance of the prepared backing member 102 is 5.5 MRayls. The prepared backing member 102 has dimensions of 11.6 mm×26 mm×12 mm. The signal FPC 104 is bonded to the rear surface side of the piezoelectric transducer. The prepared backing member 102 is bonded to the rear surface side of the signal FPC 104 (step Sb5).

The first acoustic matching layer 108 is a glass plate having a thickness of 0.4 mm and an acoustic impedance of 15 MRayls. The first acoustic matching layer 108 is bonded to the ultrasonic wave emission surface side of the piezoelectric transducer provided with electrodes. The second acoustic matching layer 110 is a carbon layer having a thickness of 0.2 mm and an acoustic impedance of 5.8 MRayls. The second acoustic matching layer 110 is bonded to the front surface side of the first acoustic matching layer 108. The ground FPC 112 is bonded to the front surface side of the second acoustic matching layer 110. The third acoustic matching layer 111 is a soft epoxy resin layer having a thickness of 0.18 mm and an acoustic impedance of 2.2 MRayls. The third acoustic matching layer 111 is bonded to the front surface side of the ground FPC (step Sb6).

The single crystal wafer having the plurality of acoustic matching layers bonded to the ground FPC is cut from the ultrasonic wave emission surface side with a width of 0.15 mm by using a dicer blade having a thickness of 50 μm (step Sb7). This cutting (array cutting) prepares the single crystal piezoelectric transducer elements 106 corresponding to a total of 96 channels. After the array cutting, a DC electric field with a voltage of 450 V (0.8 kV/mm) (an electric field lower than the pp electric field in AC polarization) is applied to each of the single crystal piezoelectric transducer elements 106 over 2 min. This executes repolarization. Note that DC polarization after array cutting may be omitted. Alternatively, DC polarization may be executed before AC polarization. In addition, the gaps produced by array cutting are sometimes partly filled with an insulating resin. The acoustic lens 114 is bonded to the front surface of the third acoustic matching layer 111 (step Sb8). With the above procedure, the ultrasonic probe 100 is manufactured.

The characteristics of the respective channels of the manufactured ultrasonic probe 100 are measured by a general method and shown by Table 8. Table 8 also shows, for comparison, the characteristics of the PMNT 71/29 piezoelectric transducers which have been polarized by applying general DC polarization with an electric field of 450 V (0.8 kV/mm) over 5 min without performing any AC polarization process for the piezoelectric transducers.

TABLE 8

|  | Capacitance (pF) | Sensitivity (mV) | Sensitivity Variation |
|---|---|---|---|
| Product Obtained by Application of DC after Application of AC | 290 | 4.5 | ±5% |
| Without AC Process | 220 | 4.0 | ±11% |

As is obvious from Table 8, the ultrasonic probe 100 obtained by applying an AC electric field to each piezoelectric transducer and then performing repolarization using a DC electric field exhibited a large channel capacitance, high sensitivity, and small variations in sensitivity as compared with the ultrasonic probe having undergone repolarization with only a DC electric field.

The transmission of ultrasonic waves using the ultrasonic probe 100 manufactured by the above manufacturing method will be described. The ultrasonic probe 100 is brought into contact with an object. A predetermined voltage is then applied between the electrode concerning the ultrasonic wave emission surface of each single crystal piezoelectric transducer element 106 and the electrode on rear side of the ultrasonic wave emission surface of each single crystal piezoelectric transducer element 106. The application of the predetermined voltage makes the single crystal piezoelectric transducer element 106 resonate to generate ultrasonic waves. The generated ultrasonic waves are transmitted to the object via the first acoustic matching layer 108, second acoustic matching layer 110, the third acoustic matching layer 111, and acoustic lens 114.

The reception of ultrasonic waves using the ultrasonic probe 100 manufactured by the above manufacturing method will be described. The ultrasonic waves generated in the object make the single crystal piezoelectric transducer element 106 vibrate via the acoustic lens 114, first acoustic matching layer 108, second acoustic matching layer 110, and third acoustic matching layer 111. The single crystal piezoelectric transducer element 106 converts the vibrations generated by ultrasonic waves into electrical signals. The electrical signals are delayed and added for the respective channels in accordance with depths in the object. The delayed/added signal is envelope-detected and logarithmically converted to be displayed as an image. It is possible to improve the transmission/reception efficiency of ultrasonic waves by setting the acoustic impedance between the first acoustic matching layer 108, the second acoustic matching layer 110, and the third acoustic matching layer 111 so as to make it gradually approach the acoustic impedance of the object between the acoustic impedance (20 to 30 MRayls) of the single crystal piezoelectric transducer element 106 and the acoustic impedance (1.5 MRayls) of the object.

Figure 12:
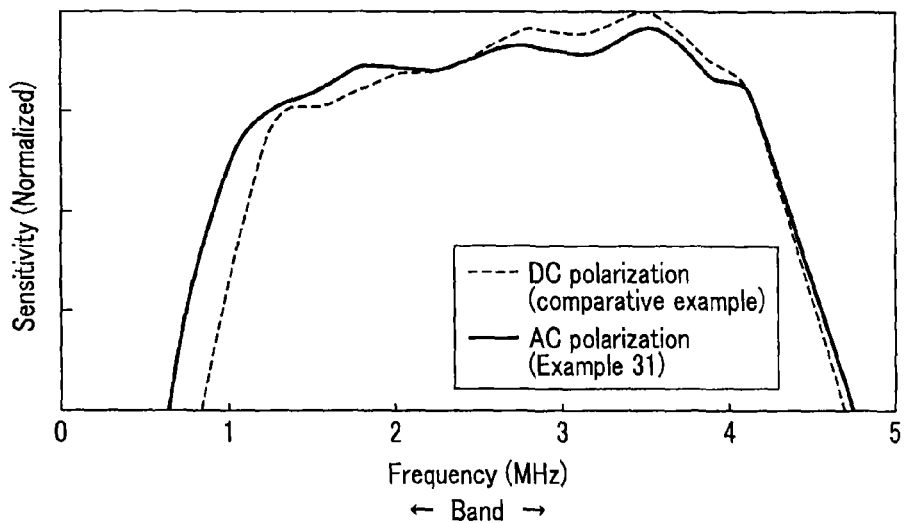
FIG. 12 is a graph showing a frequency spectrum according to this embodiment, together with a frequency spectrum according to a comparative example.

FIG. 12 is a graph showing sensitivities corresponding to frequencies (to be referred to as a frequency spectrum hereinafter) in association with the ultrasonic probe 100 (Example 31) having the piezoelectric transducer for which polarization processing using an AC electric field (to be referred to as AC polarization hereinafter) has been executed, together with a frequency spectrum according to the comparative example (the ultrasonic probe having the piezoelectric transducer to which a polarization process using a DC electric field (DC polarization) has been executed). As shown in FIG. 12, the frequency spectrum concerning the ultrasonic probe 100 according to Example 31 is wider in band and higher in sensitivity than the frequency spectrum concerning the ultrasonic probe according to the comparative example.

Figure 13:
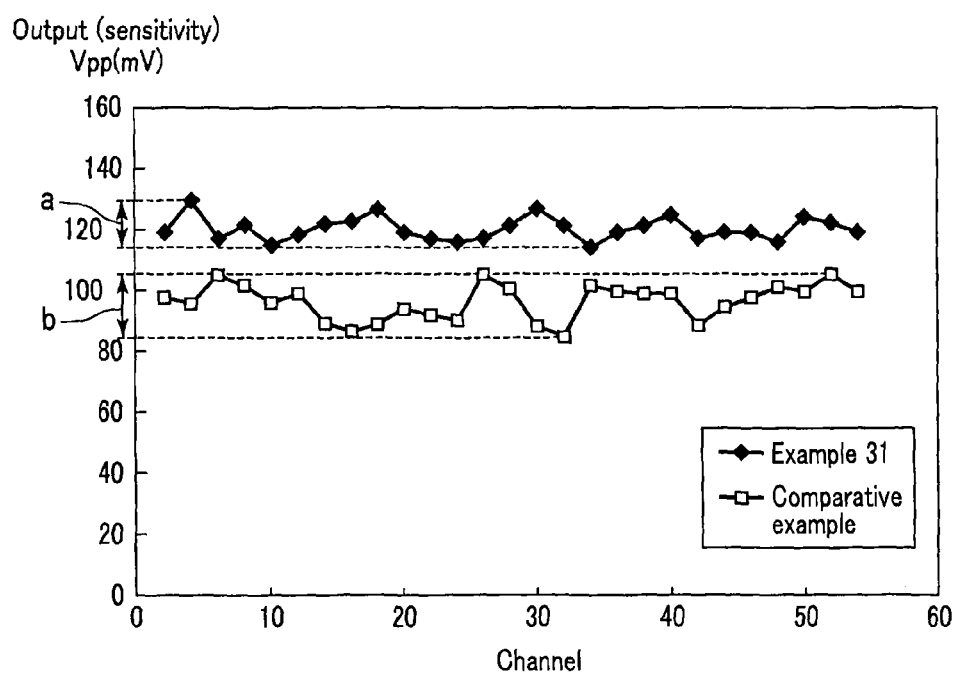
FIG. 13 is a graph showing an output (sensitivity) distribution based on a plurality of channels according to this embodiment, together with an output distribution according to a comparative example.

FIG. 13 is a graph showing an output (sensitivity) distribution based on a plurality of channels in association with the ultrasonic probe 100 (Example 4) including the piezoelectric transducer having undergone AC polarization, together with an output distribution according to a comparative example (an ultrasonic probe including a piezoelectric transducer having undergone DC polarization). As shown in FIG. 13, variations (a in FIG. 13) in output based on a plurality of channels in the ultrasonic probe 100 according to Example 31 are smaller than variations (b in FIG. 13) in output based on a plurality of channels in an ultrasonic probe according to a comparative example. In addition, outputs from the channels of the ultrasonic probe 100 according to Example 31 are larger than those from the channels of an ultrasonic probe according to a comparative example. That is, the sensitivity of the ultrasonic probe 100 according to Example 31 was 1.2 times, in average, that of the comparative example. That is, the sensitivity of the ultrasonic probe according to Example 31 improved by 20% as compared with the related art.

The following effects can be obtained by the arrangements and methods described above.

The piezoelectric transducer manufacturing method according to this embodiment can manufacture a piezoelectric transducer having a high dielectric constant and a high piezoelectric constant at a low cost in a short period of time by postprocessing (AC polarization) after the formation of a single crystal. With regard to the piezoelectric transducer prepared by this piezoelectric transducer manufacturing method or the piezoelectric transducer according to this embodiment and the ultrasonic probe according to the embodiment, in X-ray diffraction executed with the Miller index (400) with respect to the AC-polarized single crystal piezoelectric body and unpolarized single crystal piezoelectric body, the FWHM ratio falls within the range of 0.22 or more and 0.4 or less. In addition, the second FWHM is 0.1° or more and 0.2° or less. The diffraction angle ratio falls within the range of 1.0005 or more and 1.005 or less.

According to the ultrasonic probe manufacturing method according to this embodiment, it is possible to prepare an ultrasonic probe by using a piezoelectric transducer having a high dielectric constant and a high piezoelectric constant. The sensitivity of the ultrasonic probe manufactured by the ultrasonic probe manufacturing method according to the embodiment or of the ultrasonic probe according to the embodiment improves as compared with an ultrasonic probe using a piezoelectric transducer polarized by DC polarization. Variations in characteristics (sensitivity and output) between the channels in the ultrasonic probe according to the embodiment are reduced as compared with an ultrasonic probe using a piezoelectric transducer polarized by DC polarization. In addition, the frequency band associated with the ultrasonic probe according to the embodiment is wider than that associated with an ultrasonic probe using a piezoelectric transducer polarized by DC polarization. Furthermore, since the dielectric loss decreases, the heat generated when the ultrasonic probe is driven decreases. For the above reasons, using the ultrasonic probe according to the embodiment can improve the diagnostic performance. Note that the use of the piezoelectric transducer according to the embodiment is not limited to the ultrasonic probe 100 according to Example 31. This piezoelectric transducer can be applied to, for example, a sonar, nondestructive inspection apparatus, actuator, and energy harvesting element.

The phase transition temperature trm in this embodiment is limited to 80° C. to 150° C. for the following reasons. If the phase transition temperature is 80° C. or lower, the rate of change in dielectric constant at room temperature to 70° C. is large, resulting in a problem in terms of the stability of probe sensitivity. In addition, with a material having Trm equal to or higher than 150° C., even if AC polarization is performed, an improvement in dielectric constant or piezoelectric characteristic at near room temperature is as small as 10% or less.

According to this embodiment, the dielectric constants of a plurality of single crystal piezoelectric transducer elements prepared by dicing can be uniformly set within a predetermined range by adjusting a pp value and the number of times of application in AC polarization. In addition, since the diffraction angle ratio falls within the range of 1.0005 or more and 1.005 or less, the thickness of each piezoelectric transducer decreases. Along with this, the volume of each piezoelectric transducer is constant, and hence the area of each surface provided with the electrode increases. In addition, the FWHM ratio range, the second FWHM range, and the diffraction angle ratio range described in the embodiment do not appear in DC polarization.

Note that it is easily expected that an FWHM ratio and a diffraction angle ratio as technical features of this embodiment appear in not only the above (PIN)-PMN-PT-based materials but also lead-based piezoelectric single crystal materials such as lead zinc niobate (PZN)-based materials and lead scandium niobate (PSN) and non-lead-based piezoelectric materials having similar structures such as barium titanate and potassium niobate-sodium single crystals, bismuth scandium single crystal, and bismuth iron compound.

It is therefore possible to apply this method to these materials. In addition, the polarization method according to the embodiment can be applied to oriented thick films, ceramics, ceramics with large particle sizes, and composite materials containing resins including them. As has been described above, the method according to the embodiment can greatly improve the dielectric constant and piezoelectric constant of a piezoelectric material at a low cost by using an AC power supply, and hence has very high industrial importance.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A piezoelectric transducer comprising:
a polarized single crystal piezoelectric body comprising a lead complex perovskite compound containing niobium oxide and at least one of magnesium oxide and indium oxide and including a first plane whose crystal orientation is [100] and a second plane which faces the first plane and whose crystal orientation is [100]; and
a first electrode provided on the first plane side of the single crystal piezoelectric body and a second electrode provided on the second plane side of the single crystal piezoelectric body,
wherein a ratio of a second FWHM of diffracted X-rays at the Miller index (400) of the single crystal piezoelectric body to a first FWHM of diffracted X-rays at the miller index (400) of the single crystal piezoelectric body which is unpolarized or has undergone depolarization processing is not less than 0.22 and not more than 0.4.

2. The piezoelectric transducer according to claim 1, wherein a ratio of a second diffraction angle at which diffracted X-rays at the Miller index (400) of the single crystal piezoelectric body reaches a peak to a first diffraction angle at which diffracted X-rays at the miller index (400) of the single crystal piezoelectric body which is unpolarized or has undergone depolarization processing reaches a peak is not less than 1.0005 and not more than 1.005.

3. The piezoelectric transducer according to claim 1, wherein the lead complex perovskite compound contains x mol % (wherein x is a positive value) of lead titanate and (1−x) mol % of lead magnesium niobate, x=not less than 26 and not more than 33, and a phase transition temperature of a crystal structure of the lead complex perovskite compound is not less than 80° C. and not more than 150° C.

4. The piezoelectric transducer according to claim 1, wherein the lead complex perovskite compound contains z mol % (wherein z is a positive value) of lead indium niobate, y mol % (wherein y is a positive value) of lead magnesium niobate, and x mol % of lead titanate, x=not less than 26 and not more than 33, y=not less than 24 and not more than 59, z=not less than 15 and not more than 50, and x+y+z=100.

5. The piezoelectric transducer according to claim 2, wherein an FWHM of an X-ray intensity distribution corresponding to the second diffraction angle is not less than 0.1° and not more than 0.2°.

6. A ultrasonic probe comprising:
a polarized single crystal piezoelectric body comprising a lead complex perovskite compound containing niobium oxide and at least one of magnesium oxide and indium oxide and including a first plane whose crystal orientation is [100] and a second plane which faces the first plane and whose crystal orientation is [100];
a first electrode provided on the first plane side of the single crystal piezoelectric body and a second electrode provided on the second plane side of the single crystal piezoelectric body;
an acoustic matching layer provided on a front surface of the first electrode; and
a backing member provided on a rear surface of the second electrode,
wherein a ratio of a second FWHM of diffracted X-rays at the Miller index (400) of the single crystal piezoelectric body to a first FWHM of diffracted X-rays at the miller index (400) of the single crystal piezoelectric body which is unpolarized or has undergone depolarization processing is not less than 0.22 and not more than 0.4.

7. A piezoelectric transducer manufacturing method comprising:
preparing a piezoelectric single crystal comprising a lead complex perovskite compound containing niobium oxide and at least one of magnesium oxide and indium oxide;
preparing a single crystal wafer including a first plane whose crystal orientation is [100] and a second plane which faces the first plane and whose crystal orientation is [100] by cutting the piezoelectric single crystal along a plane whose crystal orientation of the piezoelectric single crystal is [100];
providing a first electrode and a second electrode on the first plane side and the second plane side, respectively; and
applying an AC electric field between the first electrode and the second electrode.

8. The piezoelectric transducer manufacturing method according to claim 7, wherein as the AC electric field, a peak-to-peak electric field of not less than 0.5 kV/mm and not more than 3.6 kV/mm and an AC electric field having a predetermined frequency are applied a predetermined number of times.

9. The piezoelectric transducer manufacturing method according to claim 7, wherein a DC electric field in a range of not less than 0.25 kV/mm and not more than 2.5 kV/mm is applied between a first electrode and a second electrode over not less than 1 sec and not more than 30 min before and after application of the AC electric field.

10. The piezoelectric transducer manufacturing method according to claim 8, wherein the predetermined frequency is not less than 0.1 Hz and not more than 1 kHz,
the predetermined number of times is not less than 2 and not more than 1,000, and
the peak-to-peak electric field is higher than the DC electric field.

11. The piezoelectric transducer manufacturing method according to claim 9, wherein the peak-to-peak electric field is not less than 0.8 kV/mm and not more than 2.0 kV/mm, and
the DC electric field is not less than 0.5 kV/mm and not more than 1.2 kV/mm.

12. The piezoelectric transducer manufacturing method according to claim 8, wherein application of the AC electric field is executed at a temperature lower than a phase transition temperature of the lead complex perovskite compound.

* * * * *

UNITED STATES PATENT AND TRADEMARK OFFICE
CERTIFICATE OF CORRECTION

PATENT NO. : 9,972,766 B2
APPLICATION NO. : 14/840115
DATED : May 15, 2018
INVENTOR(S) : Yohachi Yamashita et al.

Page 1 of 1

It is certified that error appears in the above-identified patent and that said Letters Patent is hereby corrected as shown below:

On the Title Page

Item (63), the Related U.S. Application Data Information has been omitted. Item (63) should read:
--Related U.S. Application Data
(63) Continuation of application No. PCT/JP2014/058013, filed on Mar. 24, 2014--

Signed and Sealed this
Fourth Day of June, 2019

Andrei Iancu
*Director of the United States Patent and Trademark Office*